(12) United States Patent
Ghosh et al.

(10) Patent No.: US 8,750,994 B2
(45) Date of Patent: Jun. 10, 2014

(54) MORPHOLOGY-BASED DISCRIMINATION ALGORITHM BASED ON RELATIVE AMPLITUDE DIFFERENCES AND CORRELATION OF IMPRINTS OF ENERGY DISTRIBUTION

(75) Inventors: Subham Ghosh, Blaine, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/562,039

(22) Filed: Jul. 30, 2012

(65) Prior Publication Data

US 2013/0030481 A1 Jan. 31, 2013

Related U.S. Application Data

(60) Provisional application No. 61/513,649, filed on Jul. 31, 2011.

(51) Int. Cl.
*A61N 1/36* (2006.01)

(52) U.S. Cl.
USPC .......................................................... 607/14

(58) Field of Classification Search
USPC .......................................................... 607/14
See application file for complete search history.

(56) References Cited

U.S. PATENT DOCUMENTS

| | | | |
|---|---|---|---|
| 4,375,817 A | 3/1983 | Engle et al. | |
| 4,384,535 A | 5/1983 | McKelvie | |
| 4,548,209 A | 10/1985 | Wielders et al. | |
| 4,577,633 A | 3/1986 | Berkovits et al. | |
| 4,587,970 A | 5/1986 | Holley et al. | |
| 4,693,253 A | 9/1987 | Adams | |
| 4,727,380 A | 2/1988 | Miura et al. | |
| 4,800,883 A | 1/1989 | Winstrom | |
| 4,819,643 A | 4/1989 | Menken | |
| 4,830,006 A | 5/1989 | Haluska et al. | |
| 4,880,004 A | 11/1989 | Baker, Jr. et al. | |
| 4,880,005 A | 11/1989 | Pless et al. | |
| 4,949,719 A | 8/1990 | Pless et al. | |
| 4,949,730 A | 8/1990 | Cobben et al. | |
| 4,953,551 A | 9/1990 | Mehra et al. | |
| 4,974,598 A | 12/1990 | John | |
| 5,117,824 A | 6/1992 | Keimel et al. | |
| 5,163,427 A | 11/1992 | Keimel | |
| 5,188,105 A | 2/1993 | Keimel | |
| 6,249,701 B1 | 6/2001 | Rajasekhar et al. | |
| 6,393,316 B1 | 5/2002 | Gillberg et al. | |

(Continued)

OTHER PUBLICATIONS

William Mendenhall, Statistics For Engineering and The Sciences 4th ed. pp. 221-228 (1995).

*Primary Examiner* — George Manuel
(74) *Attorney, Agent, or Firm* — Carol F. Barry

(57) ABSTRACT

Techniques for morphologic discrimination between beats of a tachyarrhythmia episode are described for selecting delivery of appropriate therapy. An exemplary method comprises nonordered binning of digitized amplitude values of signals associated with cardiac depolarizations. Monomorphic VT is discriminated from polymorphic VT without signal alignment. One exemplary method involves sensing electrical signals associated with depolarizations of a patient's heart during a tachyarrhythmia episode. The sensed electrical signals are converted to digital values and stored. The stored digital values are normalized and binned. At most, 5 pairs of beats or depolarizations are compared for morphologic similarity by determining the similarity between the binned values associated with each pair. The result of the comparison is used to select and deliver therapy to the patient.

40 Claims, 12 Drawing Sheets

(56) References Cited

U.S. PATENT DOCUMENTS

| | | |
|---|---|---|
| 7,130,677 B2 | 10/2006 | Brown et al. |
| 7,184,835 B2 * | 2/2007 | Kramer et al. ................ 607/9 |
| 7,286,876 B2 * | 10/2007 | Yonce et al. ................ 607/28 |
| 7,447,540 B1 | 11/2008 | Nabutovsky et al. |
| 7,726,380 B2 | 6/2010 | Hirata et al. |

* cited by examiner

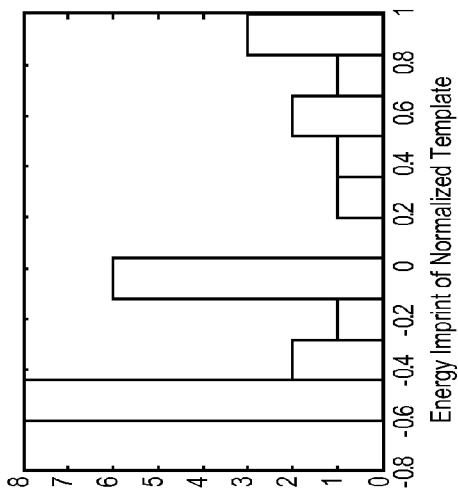
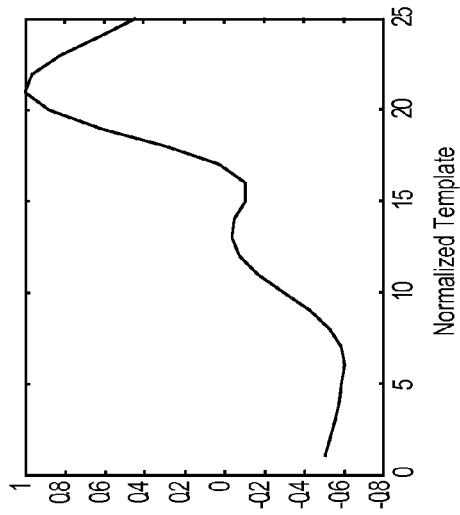
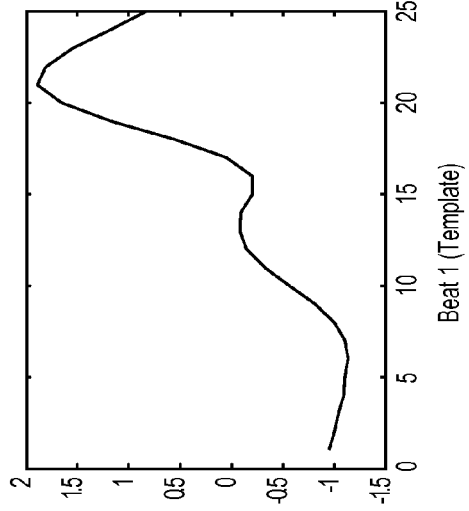
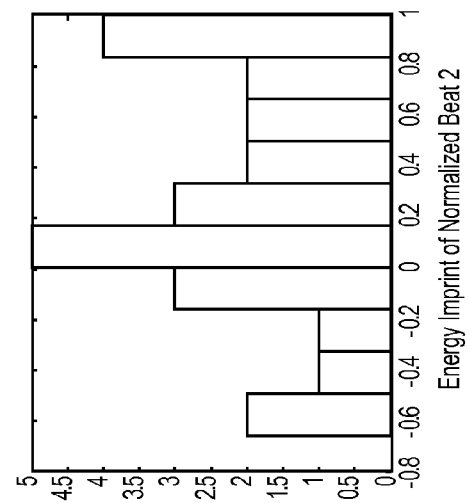
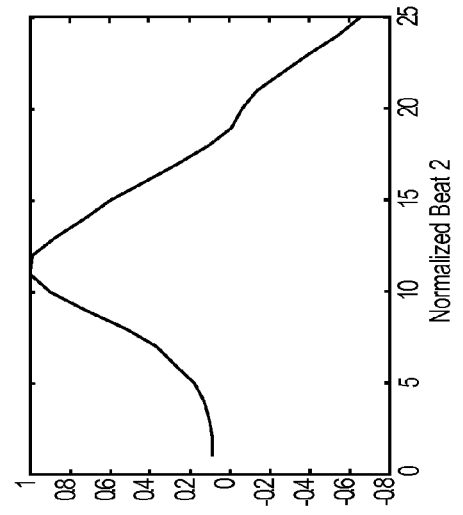
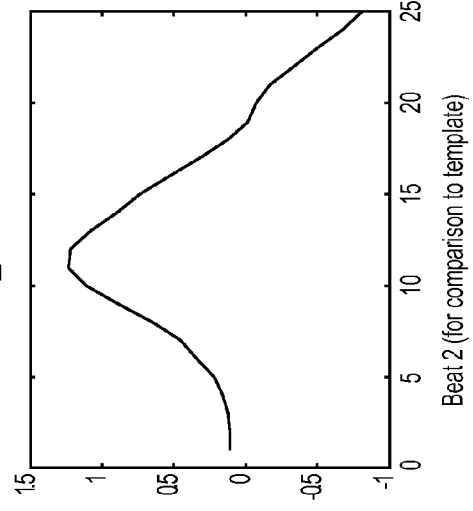

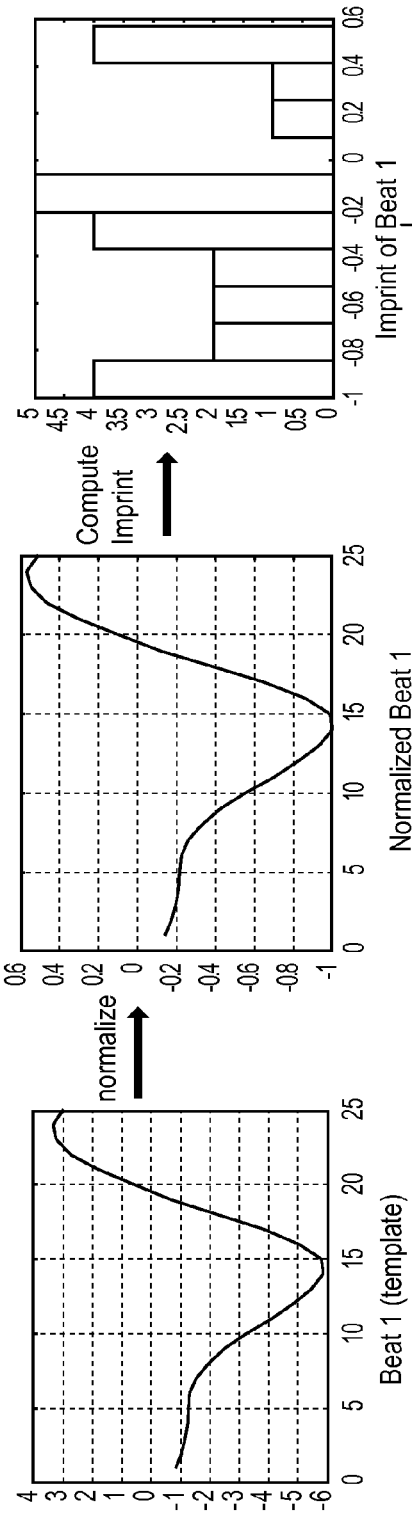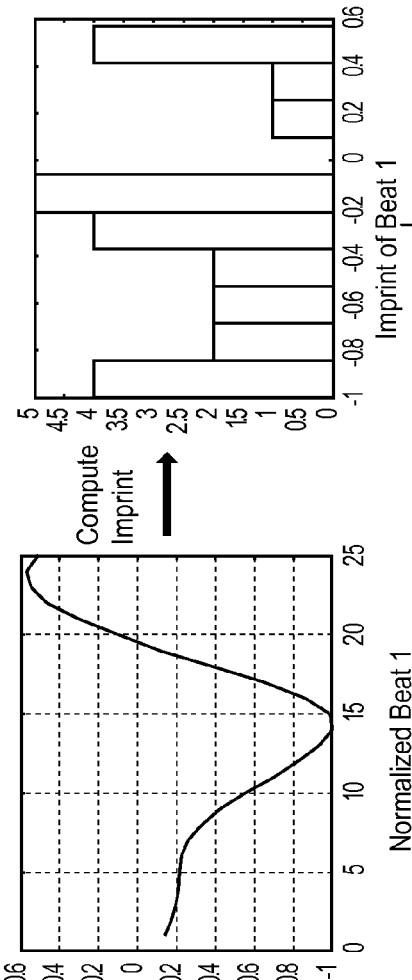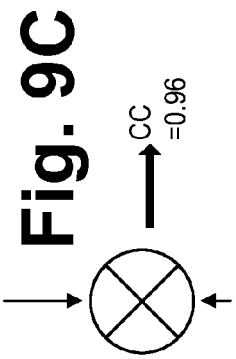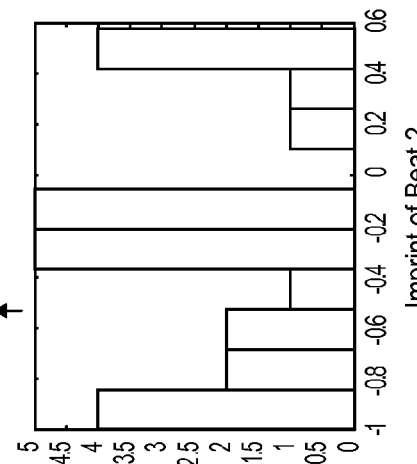

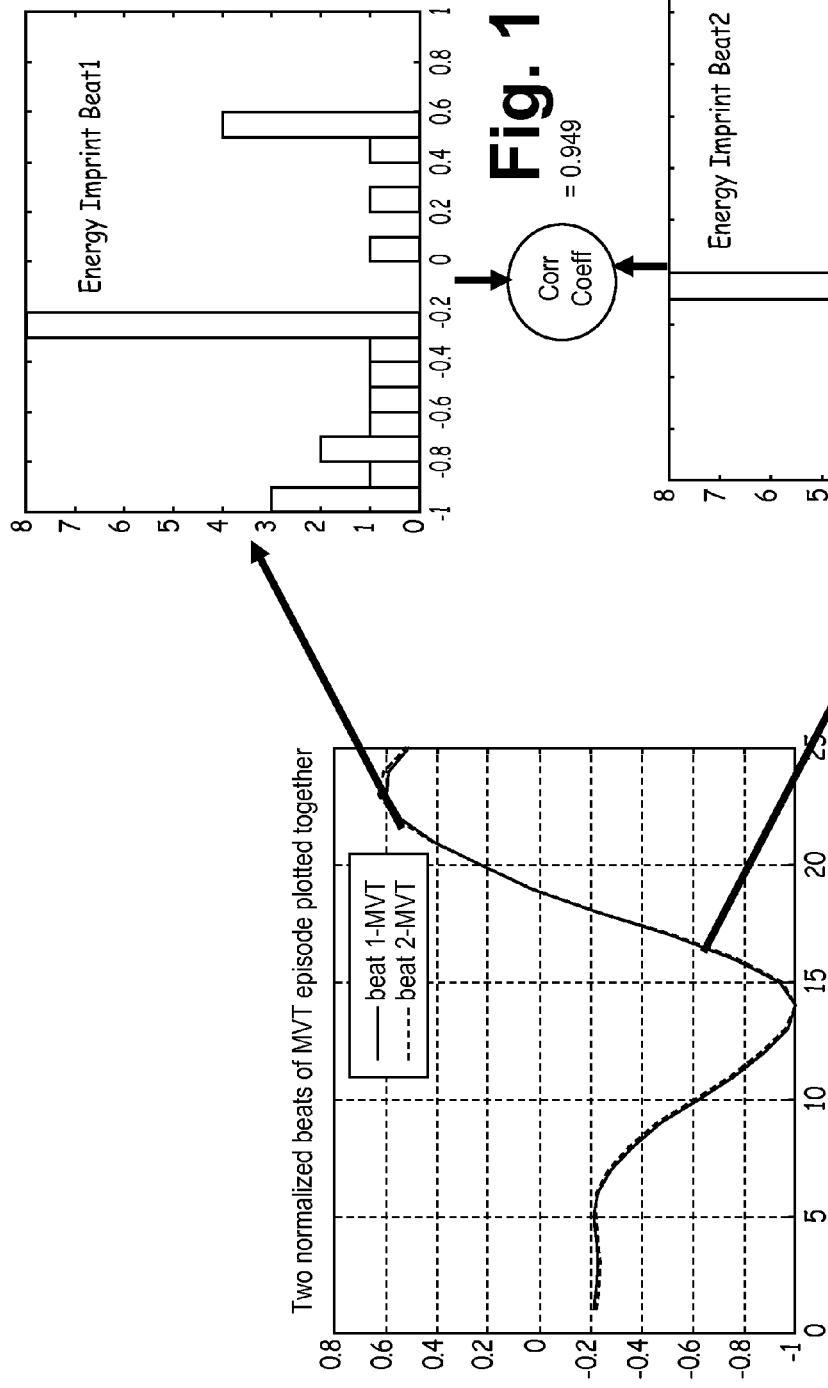

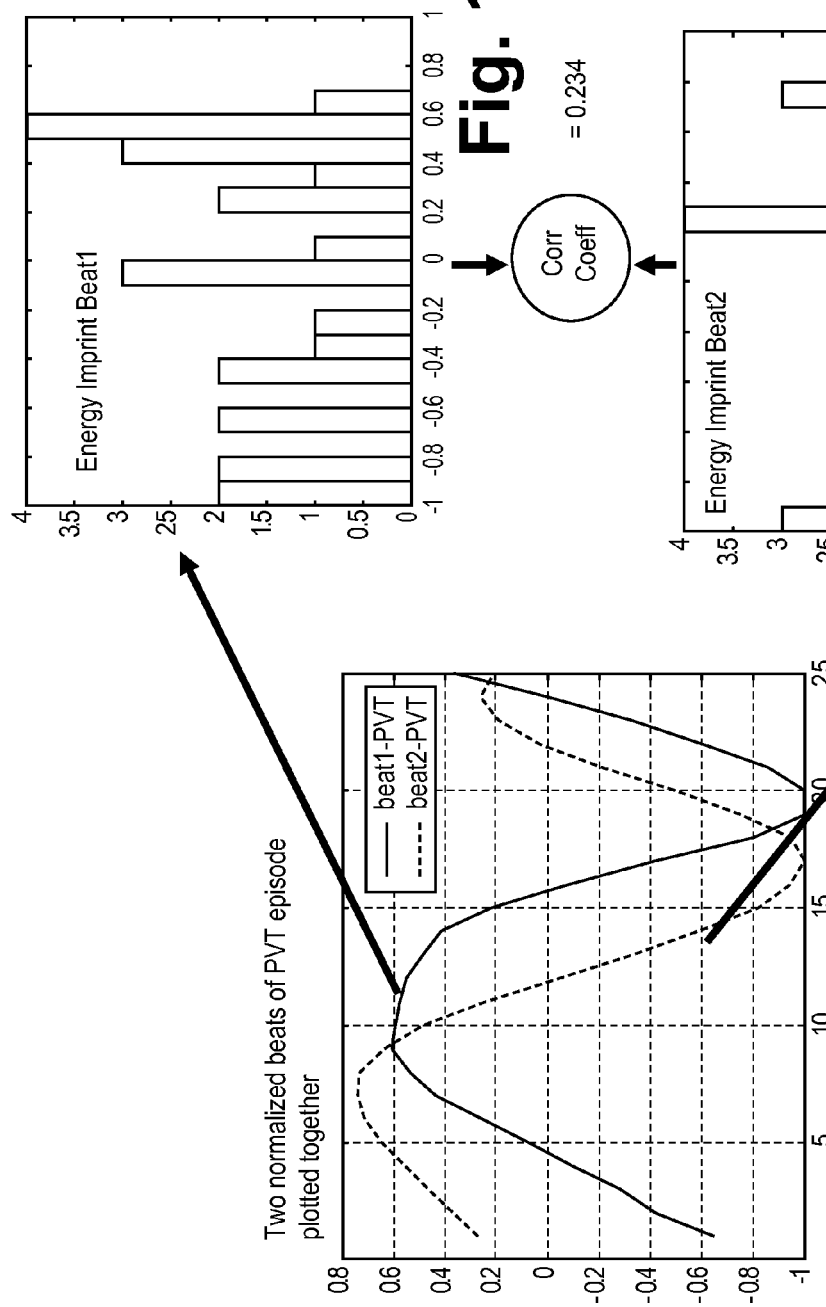

MORPHOLOGY-BASED DISCRIMINATION ALGORITHM BASED ON RELATIVE AMPLITUDE DIFFERENCES AND CORRELATION OF IMPRINTS OF ENERGY DISTRIBUTION

CROSS-REFERENCE TO RELATED APPLICATIONS

This application claims the benefit of U.S. Provisional Application No. 61/513,649, filed on Jul. 31, 2011. The disclosure of the above application is incorporated herein by reference in its entirety.

TECHNICAL FIELD

The present disclosure relates to implantable monitors and stimulators generally, and, more particularly, to implantable heart monitors and heart stimulators, such as implantable cardioverter/defibrillators (ICDs).

BACKGROUND

While implantable ICDs frequently deliver life saving therapy, occasionally an unnecessary electrical shock can be delivered to a patient's heart in response to rapid heart rates caused by exercise (e.g. sinus tachycardia) or by atrial fibrillation. Such rhythms, known collectively as supraventricular tachycardias (SVTs), may occur in up to 30% of ICD patients.

Anti-tachycardia pacing (ATP), a painless therapy, can be used to substantially terminate many monomorphic VTs without delivering unnecessary electrical shocks. While ATP is painless, ATP may not deliver effective therapy for all types of VTs. For example, ATP may not be as effective for polymorphic VTs, which is a fast rhythm (VTs) with variable morphologies. Polymorphic VTs and ventricular fibrillation (VFs) can be more lethal and require expeditious treatment by shock. The morphology of the QRS complex in the electrogram (EGM) signal may be used to discriminate a SVT episode from a VT episode or a monomorphic VT episode from a polymorphic VT episode. In the first case, the EGM morphology of each beat of an episode is compared to the morphology of a sample waveform recorded from the normal heartbeat, typically referred to as the template. In the second case, the morphology of each beat of a VT episode may be compared to that of one or more different beats from the same episode, which serve(s) as the template(s). One morphological method to discriminate between an episode beat and a template beat is based on wavelet comparison. A template beat is either a normal beat or another beat from the same episode. An exemplary wavelet comparison method may be seen with respect to U.S. Pat. No. 6,393,316 issued May 21, 2002. Generally, the wavelet comparison method involves aligning the EGM signal with the template signal based on certain characteristics (e.g. peaks or valleys), transforming the digitized signal into signal wavelet coefficients, then identifying higher amplitude digitized signals of the signal wavelet coefficients. Thereafter, a match metric is generated that corresponds to the higher amplitude digitized signals of the signal wavelet coefficients. A corresponding set of template wavelet coefficients is derived from signals indicative of a heart depolarization of known type.

While the wavelet comparison method successfully eliminates or substantially reduces unnecessary electrical shocks delivered to a patient's heart, the wavelet comparison method requires shifting and alignment of the episode beat to the template beat for accurate morphologic discrimination. Shifting and alignment of the episode beat to the template beat may be computationally expensive, especially for monomorphic versus polymorphic VT discrimination in which more than one template beats derived from the same episode may be needed for comparison. Thus, it may be beneficial to develop additional or alternative methods that are able to distinguish SVT from VT or monomorphic VT from polymorphic VT.

BRIEF DESCRIPTION OF DRAWINGS

FIG. 7A is a graph of a weighted depolarization template from a polymorphic VT episode.

FIG. 7B is a graph of a normalized depolarization of the weighted depolarization from FIG. 7A.

FIG. 7C is a graph of an energy imprint of the normalized depolarization depicted in FIG. 7B.

FIG. 8A is a graph of another weighted depolarization from a polymorphic VT episode that is to be compared to the beat template of FIG. 7A.

FIG. 8B is a graph of a normalized depolarization depicted in FIG. 8A.

FIG. 8C is a graph of an energy imprint of the normalized depolarization depicted in FIG. 8B.

FIG. 9A is a graph of a weighted depolarization template from a monomorphic VT episode.

FIG. 9B is a graph of a normalized depolarization template of FIG. 9A.

FIG. 9C is a graph of a normalized energy imprint created from the normalized depolarization template shown in FIG. 9B.

FIG. 10A is a graph of a weighted depolarization from a monomorphic VT episode that is to be compared to the beat template of FIG. 9A.

FIG. 10B is a graph of a normalized depolarization of the weighted depolarization shown FIG. 10A.

FIG. 10C is a graph of a normalized energy imprint created from the normalized depolarization shown in FIG. 10B.

FIG. 11A is a graph of first and second normalized depolarizations of a monomorphic VT episode.

FIG. 11B is a graph of an energy imprint of the first depolarization depicted in FIG. 11A.

FIG. 11C is a graph of an energy imprint of the second depolarization depicted in FIG. 11A.

FIG. 12A is a graph of two normalized depolarizations of a polymorphic VT episode.

FIG. 12B is a graph of an energy imprint of the first depolarization depicted in FIG. 12A.

FIG. 12C is a graph of an energy imprint of the second depolarization depicted in FIG. 12A.

DETAILED DESCRIPTION

Figure 1:
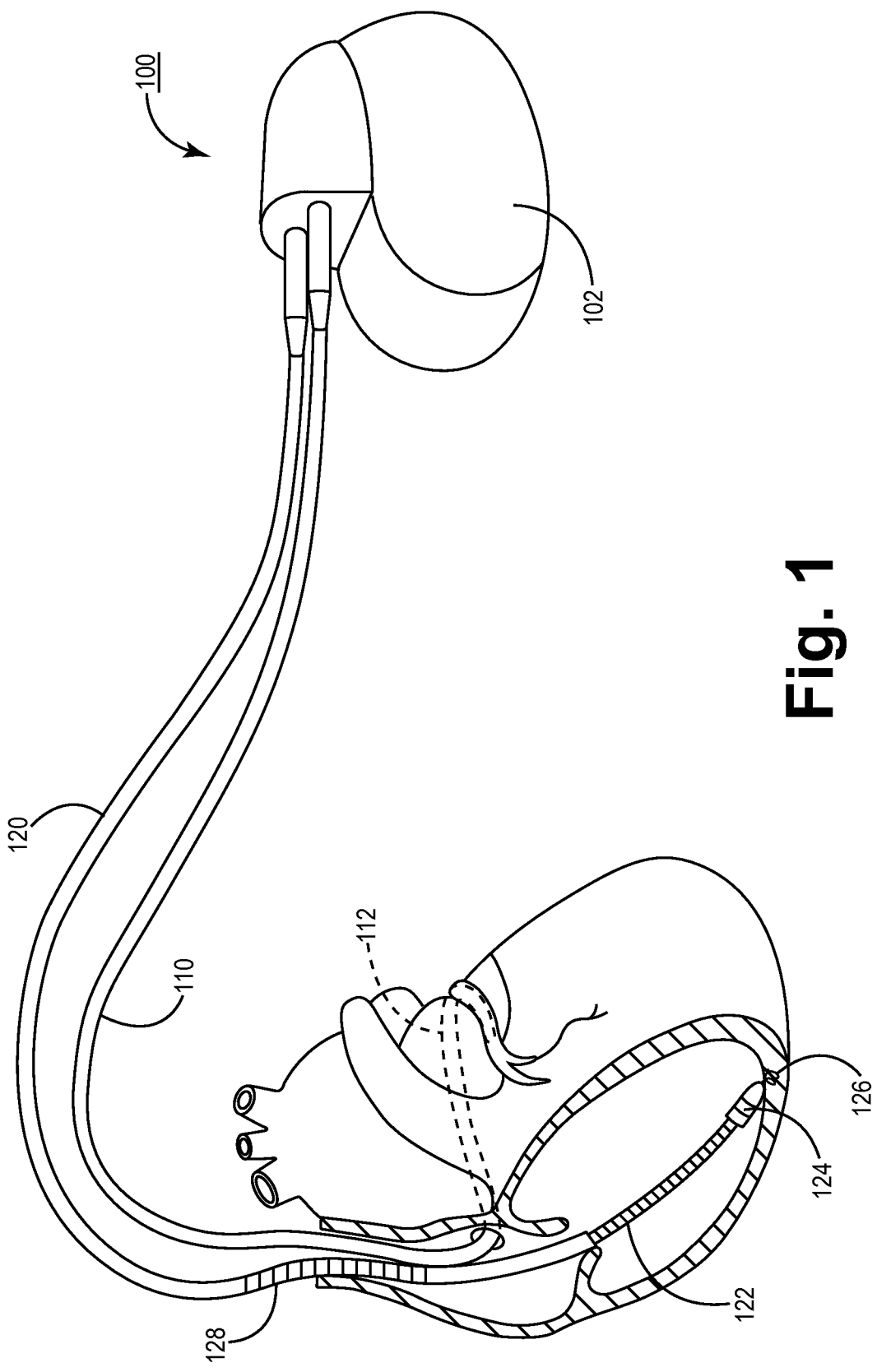
FIG. 1 is a schematic of a transvenous/subcutaneous electrode system in conjunction with a pacemaker/cardioverter/defibrillator embodying the present disclosure.

The present disclosure comprises a method and apparatus for reliable discrimination of monomorphic ventricular tachycardia (VT) from polymorphic VT/VF or discrimination of SVT from VT. An exemplary embodiment relates to an implantable medical device (IMD) that senses electrical signals associated with at least first and second depolarizations of a patient's heart. The sensed electrical signals are converted to digital values which are stored in the memory of the IMD. The stored digital values of the first and second depolarizations are normalized and then binned. The first depolarization refers to the beat of a tachyarrhythmia episode. The second depolarization refers to another beat of the same tachyarrhythmia episode or to a previously recorded beat indicative of a depolarization of known type. The binned values associated with the first depolarization are compared to the binned values associated with the second depolarization. N number of beat-pair comparisons are made where N≤5, and the result of the comparison is used to select and deliver appropriate therapy to the patient. For example, painless anti-tachycardia pacing is delivered to treat monomorphic VT while shock is delivered to treat polymorphic VT.

One or more embodiments involve a method of morphologic discrimination of heart beats of a tachyarrhythmia episode without shifting and aligning the normalized digital signal values associated with the beats to a template derived from signals indicative of a heart depolarization of a known type or from a different beat chosen from within the same tachyarrhythmia episode. Elimination of shifting and aligning the normalized digital values associated with the heart beats reduces the number of clock cycles used to determine whether therapy is needed. Reducing the number of clock cycles that need to be processed to identify and determine the type of VT present in a patient can reduce energy consumption and potentially extend battery life. Additionally, fewer comparisons between depolarizations or heartbeats need to be performed in order to determine the type of VT present in a patient. In one exemplary embodiment, only five comparisons between depolarizations needs to be performed to reliably discriminate monomorphic VT from polymorphic VT/VF or discriminate SVT from VT. Moreover, the present disclosure may be used for beat-to-beat monitoring of energy imprint matches to determine morphological changes in rhythm.

One or more embodiments relates to a method of treating heart rhythms. The method includes sensing electrical signals associated with depolarizations of a patient's heart. The sensed electrical signals are converted to digital values and storing the digital values. The stored digital values associated with at least a pair of depolarizations of the patient's heart are normalized. The normalized digital values associated with the depolarizations are binned. The binned values associated with one depolarization are compared to the binned values associated with another depolarization in the pair of depolarizations. A result of the comparison is used to select and deliver a therapy. The details of one or more aspects of the disclosure are set forth in the accompanying drawings and the description below. Other features, objects, and advantages will be apparent from the description and drawings, and from the claims.

FIG. 1 illustrates an implantable pacemaker/cardioverter/defibrillator 100 and its associated lead system, as implanted in and adjacent to the heart. As illustrated, the lead system comprises a coronary sinus lead 110, a right ventricular lead 120, and a subcutaneous lead (not shown). The coronary sinus lead is provided with an elongated electrode located in the coronary sinus and great vein region at 112, extending around the heart until approximately the point at which the great vein turns downward toward the apex of the heart. The right ventricular lead 120 includes two elongated defibrillation electrodes 122 and 128, a ring electrode 124, and helical electrode 126, which is screwed into the tissue of the right ventricle at the right ventricular apex. The right ventricular lead 120 can be used to sense electrical signals (e.g. heart beats etc.) from the patient's heart. The housing 102 of defibrillator 100 may serve as an additional electrode.

In conjunction with the present disclosure, the lead system illustrated provides electrodes that may be used to detect electrical activity in the ventricles, for example, ring electrode 124 and tip electrode 126 may be used to detect the occurrence of an R-wave and ring electrode 124 and subcutaneous defibrillation electrode (not shown) may be used to provide an EGM signal stored in response to R-wave detect. Onset of EGM signals that are stored begins when three intervals of abnormal arrhythmia is detected and stops storing when eight consecutive non-arrhythmia beats are detected. Alternatively, electrodes 124 and 126 may be used for both R-wave detection and as a source for the stored digitized EGM signal used for morphology analysis. In one or more embodiments, a far field EGM signal can be obtained. Other electrode configurations may also be employed. In alternative embodiments in which atrial depolarizations are of interest, sensing electrodes would correspondingly be placed in or adjacent the patients atria.

In one or more other embodiments, a computer program can be configured to periodically store in memory sensed data (e.g. related to a sensed depolarization etc.). Computer instructions for storing data can be part of IMD's firmware or another computer program that is executed separately or integrated with computer instructions that are generally presented in the flow diagrams described herein.

Figure 2:
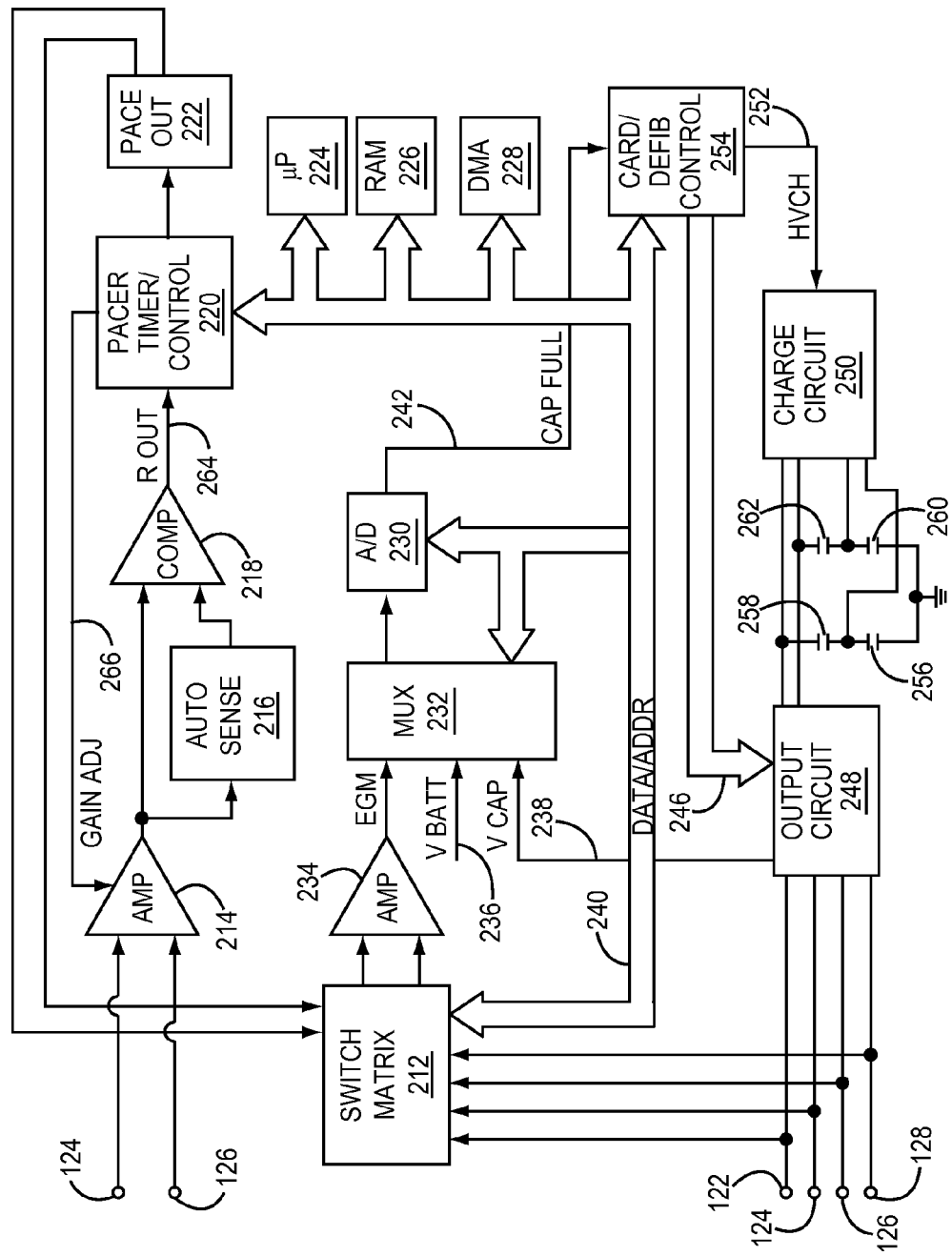
FIG. 2 is a functional schematic diagram illustrating the structure of one embodiment of an implantable pacemaker/cardioverter/defibrillator in which the present disclosure may be embodied.

FIG. 2 is a functional schematic diagram of an implantable/pacemaker/cardioverter/defibrillator in which the present disclosure may usefully be practiced. FIG. 2 is exemplary of the type of device in which the present disclosure may be embodied, and not as limiting, as it is believed that the present disclosure may usefully be practiced in a wide variety of device implementations, including devices having functional organization similar to any of the implantable pacemaker/defibrillator/cardioverters presently being implanted for clinical evaluation in the United States. The present disclosure is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, U.S. Pat. No. 6,393,316, issued to Gillberg et al. on May 21, 2002 all of which are incorporated herein by reference in their entireties.

The device is illustrated as being provided with electrodes 122, 124, 126, 128. Electrodes 124 and 126 may be a pair of electrodes located in the ventricle shown in FIG. 1. Electrodes 122, 128 may correspond to the large surface area defibrillation electrodes located on the ventricular and coronary sinus leads illustrated in FIG. 1 or to epicardial or subcutaneous defibrillation electrodes. It is also appreciated that the housing 102 of the implantable pacemaker/cardioverter/defibrillator can be used as a remote electrode.

Electrodes 124 and 126 are shown as hard-wired to the R-wave detector circuit. The R-wave detector circuit comprises bandpass amplifier 214, auto-threshold circuit 216 for providing an adjustable sensing threshold as a function of the measured R-wave amplitude and comparator 218. A signal is generated on R-out line 264 whenever the signal sensed between electrodes 124 and 126 exceeds the present sensing threshold defined by auto threshold circuit 216. As illustrated, the gain on the band pass amplifier 214 is also adjustable by means of a signal from the pacer timing and control circuitry 220 on GAIN ADJ line 266.

The operation of this R-wave detection circuitry may correspond to that disclosed in U.S. Pat. No. 5,117,824 by Keimel, et al., issued Jun. 2, 1992, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present disclosure.

The threshold adjustment circuit 216 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article, "Reliable R-Wave Detection from Ambulatory Subjects", by Thakor et al., published in Biomedical Science Instrumentation, Vol. 4, pp 67-72, 1978, incorporated herein by reference in its entirety. An improved version of such an amplifier is disclosed in U.S. Pat. No. 6,249,701, issued Jun. 19, 2001 by Rajasekhar, et al., for an "Implantable Device with Automatic Sensing Adjustment", also incorporated herein by reference in its entirety. The present disclosure may also be practiced in conjunction with more traditional R-wave sensors of the type comprising a band pass amplifier and a comparator circuit to determine when the band-passed signal exceeds a predetermined, fixed sensing threshold.

Switch matrix 212 is used to select which of the available electrodes for use in conjunction with the present disclosure. For example, switch matrix 212 can switch electrode 124 and/or electrode 126 from sensing to deliver therapy. Additionally, switch matrix 212 can also select which electrode pair (e.g. electrode 122, 124 or electrodes 124, and 126) are employed in conjunction with R-wave width measurement function, which is controlled by the microprocessor 224 via data/address bus 240.

Signals from the selected electrodes are passed through band-pass amplifier 234 and into multiplexer 232, where they are converted to mult-bit digital signals by A/D converter 230, for storage in random access memory 226 under control of direct memory address circuit 228. Microprocessor 224 employs the digitized EGM signal stored in random access memory 226 in conjunction with the morphology or signal analysis method of the present disclosure. For example, the microprocessor 224 may analyze the EGM stored in an interval extending from 100 milliseconds previous to the occurrence of an R-wave detect signal on line 264, until 100 milliseconds following the occurrence of the R-wave detect signal. The operation of the microprocessor 224 in performing the discrimination methods of the present disclosure is controlled by means of software stored in memory such as ROM, associated with microprocessor 224.

The remainder of the circuitry is dedicated to the provision of cardiac pacing, cardioversion and defibrillation therapies. The pacer timing/control circuitry 220 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 224, and are communicated to the pacing circuitry 220 via address/data bus 240. Pacer timing/control circuitry also determines the amplitude of the cardiac pacing pulses and the gain of band-pass amplifier, under control of microprocessor 224.

During VVI mode pacing, the escape interval counter within pacer timing/control circuitry 220 is reset upon sensing of an R-wave as indicated by a signal on line 264, and on timeout triggers generation of a pacing pulse by pacer output circuitry 222, which is coupled to electrodes 124 and 126. The escape interval counter is also reset on generation of a pacing pulse, and thereby controls the basic timing of cardiac pacing functions, including anti-tachycardia pacing. The duration of the interval defined by the escape interval timer is determined by microprocessor 224, via data/address bus 240. The value of the count present in the escape interval counter when reset by sensed R-waves may be used to measure the duration of R-R intervals, to detect the presence of tachycardia and to determine whether the minimum rate criteria are met for activation of the width measurement function.

Microprocessor 224 operates as an interrupt driven device, under control of software stored in the ROM associated with microprocessor 224 and responds to interrupts from pacer timing/control circuitry 220 corresponding to the occurrence of sensed R-waves and corresponding to the generation of cardiac pacing pulses. These interrupts are provided via data/address bus 240. Any necessary mathematical calculations to be performed by microprocessor 224 and any updating of the values controlled by pacer timing/control circuitry 220 take place following such interrupts. These calculations include those described in more detail below associated with the discrimination methods of the present disclosure.

In the event that a tachycardia is detected, and an anti-tachycardia pacing regimen is desired, appropriate timing intervals for controlling generation of antitachycardia pacing therapies are loaded from microprocessor 224 into the pacer timing and control circuitry 220, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 224 employs the counters to timing and control circuitry 220 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 224 activates cardioversion/defibrillation control circuitry 254, which initiates charging of the high voltage capacitors 256, 258, 260 and 262 via charging circuit 250, under control of high voltage charging line 252. The voltage on the high voltage capacitors is monitored via VCAP line 238, which is passed through multiplexer 232, and, in response to reaching a predetermined value set by microprocessor 224, results in generation of a logic signal on CAP FULL line 242, terminating charging.

Thereafter, delivery of the timing of the defibrillation or cardioversion pulse is controlled by pacer timing/control circuitry 220. One embodiment of an appropriate system for delivery and synchronization of cardioversion and defibrillation pulses, and controlling the timing functions related to them is disclosed in more detail in U.S. Pat. No. 5,188,105, issued to Keimel on Feb. 23, 1993 and incorporated herein by reference in its entirety. However, any known cardioversion or defibrillation pulse generation circuitry is believed usable in conjunction with the present disclosure. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of antitachycardia pacing pulses may also be used as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties.

In modern pacemaker/cardioverter/defibrillators, the particular antitachycardia and defibrillation therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. Prior art patents illustrating such preset therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present disclosure is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the present disclosure, selection of the particular electrode configuration for delivery of the cardioversion or defibrillation pulses is controlled via output circuit 248, under control of cardioversion/defibrillation control circuitry 254 via control bus 246. Output circuit 248 determines which of the high voltage electrodes 122, 128 will be employed in delivering the defibrillation or cardioversion pulse regimen, and may also be used to specify a multielectrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel on Nov. 17, 1992, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present disclosure. Alternatively single monophasic pulse regimens employing only a single electrode pair according to any of the above-cited references that disclose implantable cardioverters or defibrillators may also be used.

As discussed above, switch matrix 212 selects which of the various electrodes are coupled to band pass amplifier 234. Amplifier 234 may be a band-pass amplifier, having a band pass extending for approximately 0.5 to 200 hertz. The filtered EGM signal from amplifier 234 is passed through multiplexer 232, and digitized in A/D converter circuitry 230. The digitized EGM data is stored in random access memory 226 under control of direct memory address (DMA) circuitry 228. Preferably, a portion of RAM 226 is configured as a looping or buffer memory, which stores at least the preceding several seconds of the EGM signal.

The occurrence of an R-wave detect signal on line 264 is communicated to microprocessor 224 via data/address bus 240, and microprocessor 224 notes the time of its occurrence. If the morphology analysis function is activated, microprocessor 224 may, for example, wait 100 milliseconds or other physician selected interval following the occurrence of the R-wave detect signal, and thereafter transfer the most recent 200 milliseconds or other physician selected interval of digitized EGM stored in the looping or buffer memory portion of the random access memory circuit 226 to a second memory location, where the contents may be digitally analyzed according to the present disclosure. In this case, the transferred 200 milliseconds of stored EGM will correspond to a time window extending 100 milliseconds on either side of the R-wave detect signal. Window sizes in any case should be sufficient to allow analysis of the entire QRS complexes associated with the detected R-waves. The microprocessor 224 also updates software-defined counters that hold information regarding the beats that match a beat template. The counters are incremented on the occurrence of a match between a sensed beat and a template beat stored in memory. Skilled artisans appreciate that the template beat can be derived from signals indicative of a normal heart depolarization for a particular patient. In one or more other embodiments, template beat is determined for a particular population of patients. For example, a template beat may be an average heart beat experienced by a specified population of patients. Age, sex, weight, height, and/or blood pressure may be one or more factors considered in determining an average heart beat.

The following exemplary VT detections described herein can be employed in commercially marketed Medtronic implantable devices or other suitable implantable pacemaker/cardioverter/defibrillators. To this end, the device determines whether sensed beats matches a template beat and then associated software-defined counters track the numbers of beats that match template beats.

Figure 3:
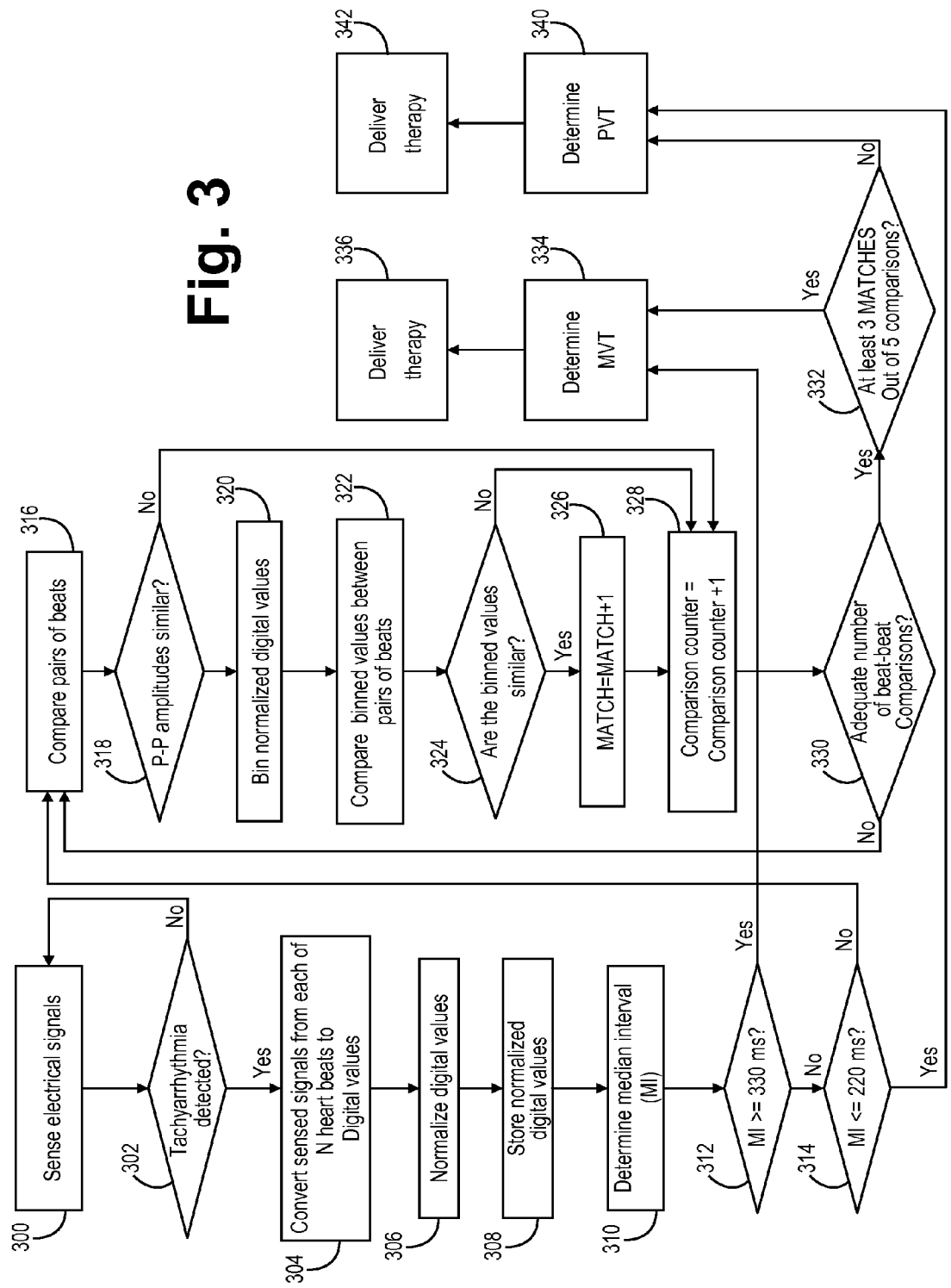
FIG. 3 is a functional flow diagram illustrating the over-all operation of tachyarrhythmia detection functions and their interrelation with the analysis function provided by the present disclosure, as embodied in a microprocessor based device as illustrated in FIG. 2.
Figure 4A:
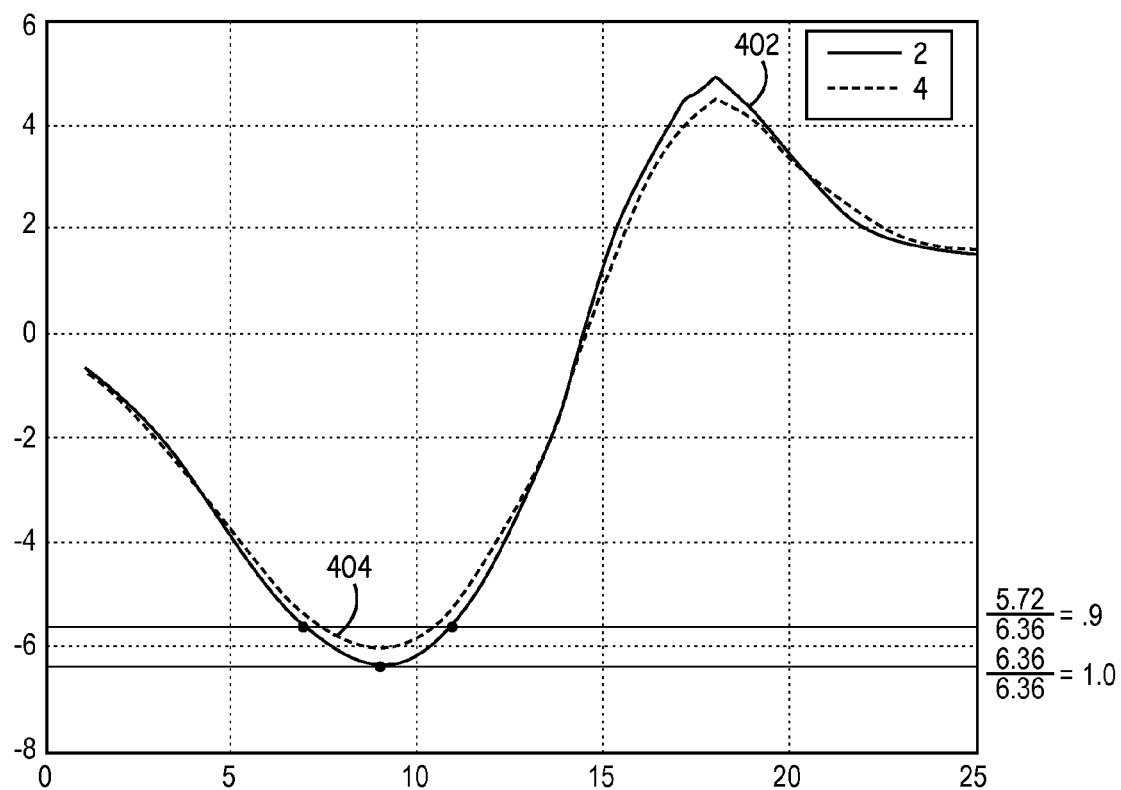
FIG. 4A is a graph of two weighted depolarizations of a monomorphic VT episode.
Figure 4B:
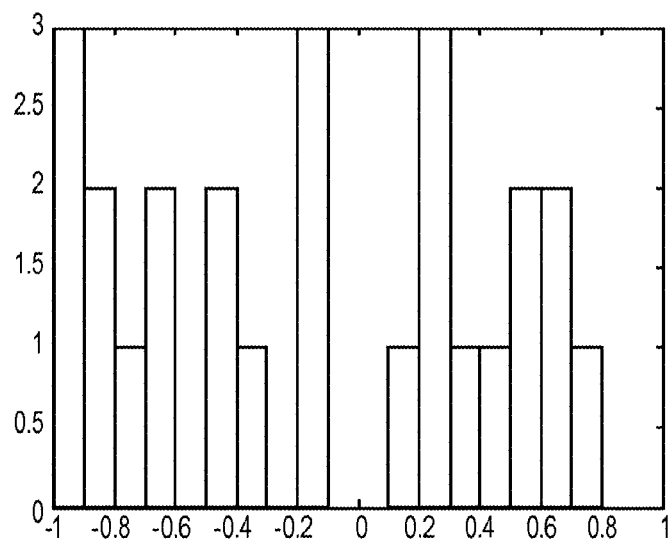
FIG. 4B is a graph of an energy imprint of the first depolarization depicted in FIG. 4A.
Figure 4C:
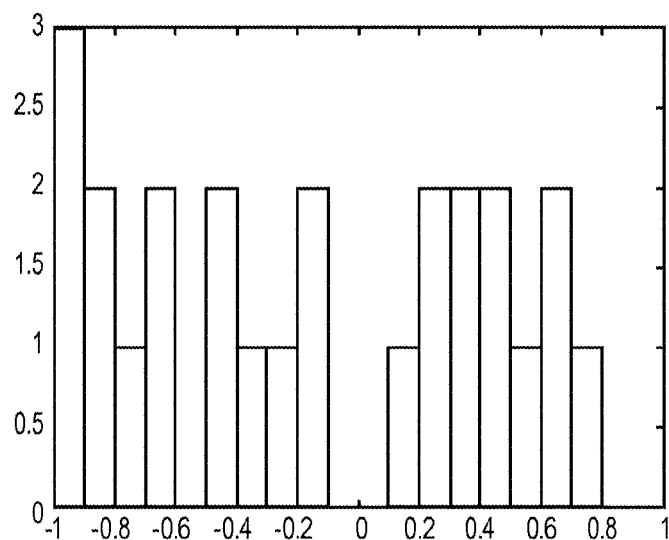
FIG. 4C is a graph of an energy imprint of the second depolarization depicted in FIG. 4A.

FIG. 3 is a functional flow diagram illustrating an exemplary over-all operation of tachyarrhythmia detection functions and their interrelation with the signal analysis function, as embodied in a microprocessor 224 illustrated in FIG. 2. In particular, FIG. 3 reliably discriminates monomorphic ventricular tachycardia (VT) from polymorphic VT/VF. One or more exemplary embodiments involves sensing electrical signals associated with depolarizations or beats of a patient's heart at block 300. Each depolarization can be sensed through one or more electrodes on the medical electrical lead depicted in FIG. 1. At block 302, a determination is made as to whether tachyarrhytmia is detected. Tachyarrhythmia is any disturbance of the heart rhythm in which the heart rate is abnormally increased resulting in short R wave to R wave intervals. For example, a 100 beats per minute (bpm) or more in a resting adult is generally considered an abnormally increased heart rate. A tachyarrhythmia is detected if a certain number (e.g. 12, 16, etc.) of consecutive beats with R wave to R wave interval less than a programmed value (e.g. tachycardia detection interval) are detected or if a certain number referred to as N1, of the lastest number (N2) of beats have R wave to R wave intervals less a pre-specified value (e.g. fibrillation detection interval). The commonly programmed values of N1 and N2 may be 18 and 24, respectively. If tachyarrhytmia is not detected, then the NO return path allows electrical signals to continue to be sensed at block 300. If tachyarrhytmia is detected, then the YES path allows the sensed electrical signals from each of N heart beats to be converted to digital values at block 304 as described above through A/D converter 230 for storage in random access memory 226. N heart beats can be any number of predetermined heart beats and is greater than 10 beats (e.g. 12 beats etc.) The depolarization digitized values includes all data points of the depolarization signal corresponding to one heart beat within a time-window of pre-defined span (e.g. 200 ms) centered about the time of sensing of that particular beat. Depolarized digital values of each beat are then normalized at block 306 such that all the data points are converted to a value between −1 and 1. The process of normalization involves determining the greater of the absolute values of the positive (i.e. maximum) and negative (i.e. minimum) peaks from among the depolarization digitized values corresponding to a heart beat and dividing each of the depolarization digitized value by this value so that the values after the division range between −1 and +1. The process of normalizing data is described and shown in detail relative to William Mendenhall, *Statistics For Engineering and The Sciences* 4$^{th}$ ed. pp. 221-228 (1995), incorporated by reference herein in its entirety. First and second heartbeats 402, 404 or depolarizations, shown in analog form in FIG. 4A and normalized and binned in FIGS. 4B-4C provide a useful example of the normalization process. For example, the absolute value of positive peak of the signal in FIG. 4A is 4.97 and the absolute value of the negative peak is 6.36. In this case, the absolute value of the negative peak is greater; therefore, normalization comprises dividing each of the data points in FIG. 4A by 6.36 and mapped to FIGS. 4B and 4C for each beat. Therefore, −6.36 from FIG. 4A translates to −6.36/6.36=−1.0 on FIGS. 4B and 4C while −5.72 of FIG. 4A translates to −5.72/6.36=−0.9. The first bin shown on FIGS. 4B and 4C is designated between −1 and −0.9 (x-axis) with a frequency of 3 (y-axis). The frequency of 3 occurs due to two horizontal lines, drawn across FIG. 4A, that strikes the signal three times. The first horizontal line passes the minimum peak of −6.36 on FIG. 4A (translated as −6.36/6.36 to −1 on FIGS. 4B-4C as) while the second horizontal line strikes 5.72 two times (translated as 5.72/6.36) that equates to −0.9 on FIGS. 4B-4C). Such normalization may be performed in hardware by the microprocessor 224 in FIG. 2. The normalized digital values are then stored in memory (e.g. random access memory (RAM) etc.) at block 308.

At block 310, a median interval (MI) for a certain number of beats (e.g. 12 beats etc.) is determined and stored in memory which is helpful for determining the type of VT experienced by a patient. MI relates to a R-wave to R-wave (RR) period that is generally determined over 12 heart beats. A slow arrhythmia is characterized by a MI≥330 milliseconds (ms), which equates to a pace rate of that is less than or equal to 182 bpm. A fast arrhythmia is characterized a MI≤220 ms that equates to greater than or equal to 273 bpm. A running MI or a MI continuously averaged over time can be useful as part of detection or discrimination criteria.

Blocks 312-314 are useful in classifying the type of VT that a patient is experiencing. For example, at block 312, if the average MI≥330 ms, then the YES path is followed to block 334 where it is determined that a patient is experiencing monomorphic VT (MVT) based on the average MI≥330 ms. At block 336, therapy is delivered to treat MVT until a termination condition is met. A termination condition can be that the patient's heart returns to normal rhythm.

If MI is not ≥330 ms, then the NO path is followed to block 314 where a determination is made as to whether MI≤220 ms. If MI≤220 ms, then the YES path is followed to block 340 in which it is determined that the patient is experiencing polymorphic VT (PVT) and therapy is delivered at block 342. A termination condition can be that the patient's heart returns to a normal rhythm.

If MI≥220 ms at block 314, then the NO path is followed to block 316 to allow a sensed beat or depolarization (first depolarization) to be compared to another sensed beat or depolarization of the same episode (second depolarization). At block 316, the peak to peak (p-p) amplitudes of the first depolarization or beat is compared to the p-p amplitudes associated with the second depolarization. There are numerous ways in which to perform such a comparison. For example, amplitudes between the first depolarization and the second depolarization can be compared. One way to compare p-p amplitude is to subtract the maximum and minimum amplitude points from the first beat thereby leaving the p-p amplitude of the first depolarization (referred to as amplitude1). The p-p amplitude for the second depolarization (referred to as amplitude2) may be computed in a manner similar to the first depolarization. For example, amplitude1 and amplitude2 can be defined as follows:

amplitude1=maximum(beat1)−minimum(beat1)

amplitude2=maximum(beat2)−minimum(beat2)

where:
maximum(beat1) is a maximum value and minimum(beat1) is a minimum value among the digitized points for the first depolarization, and
maximum(beat2) is a maximum value and minimum(beat2) is a minimum value for the second depolarization.

The amplitude difference is determined between the p-p amplitudes of the first and second depolarizations. For example, the amplitude difference is amplitude1−amplitude2. Thereafter, the absolute value of the amplitude difference is determined and compared to 0.2 times amplitude1 or amplitude2, whichever is lesser. In the equation, the first term (absolute value of the amplitude difference) is represented by abs(amplitude1−amplitude2) and the second term is 0.2* lesser of (amplitude1, amplitude2).

Determining the absolute value of the amplitude difference and comparing the result to 0.2 times amplitude1 or amplitude2, helps to avoid inability to track significant amplitude differences from beat to beat. Significant amplitude differences from beat to beat may be discriminatory for determining the presence of PVT/VF since comparison of energy imprints normalizes amplitudes and may not track substantial amplitude differences from beat to beat.

Figure 6A:
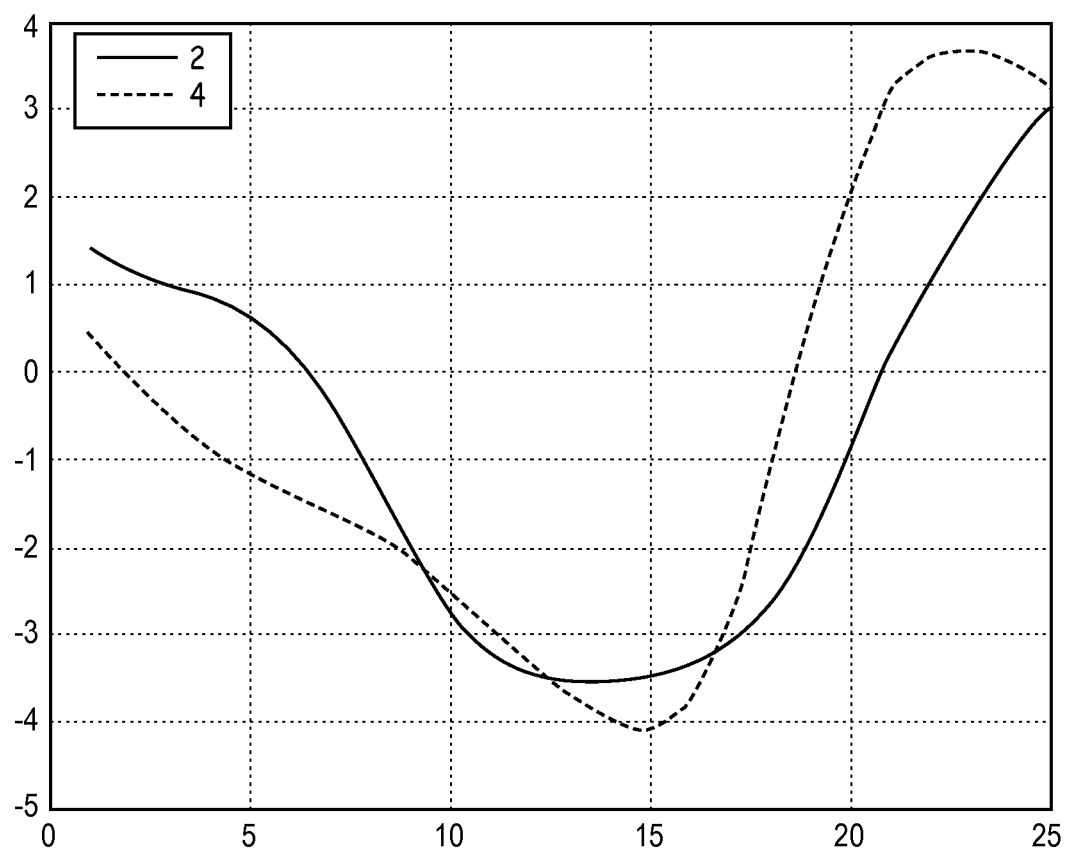
FIG. 6A is a graph of two weighted depolarizations of a polymorphic VT episode.

At block 318, if the absolute value of the difference between the peak-peak amplitudes of the depolarization signals is greater than 0.2 times the lesser of the two p-p amplitudes (amplitude 1 and amplitude 2), then the first and second depolarizations are not similar. If the p-p amplitudes are not similar, then the NO path is followed to block 328, which is discussed in greater detail below. In contrast, if the absolute value of the difference between the p-p amplitudes of the depolarization signals is not greater than 0.2 times the lesser of the two p-p amplitudes (amplitude1 or amplitude2), the p-p amplitudes are considered to be similar. The YES path is then followed to block 320 to further evaluate whether the beats are morphologically similar since two beats with similar p-p amplitudes may be morphologically different. Two beats with similar p-p amplitudes that are morphologically different is shown in FIG. 6A and described in detail below.

At block 320, the normalized digital values associated with each of the first and second depolarizations are binned in a set of bins of a histogram. A histogram graphically displays statistical information that uses rectangles to show the frequency of data in successive numerical intervals of equal size. FIG. 4B is the histogram for the template depolarization (beat 2) depicted in FIG. 4A while FIG. 4C is the histogram for the depolarization (beat 4) depicted in FIG. 4A. The histogram in FIG. 4B reflects the distribution of the data points in FIG. 4A, after normalization of amplitude or energy levels in the depolarization. A histogram of the normalized amplitudes plots a number of samples in each normalized level from a minimum of −1 to a maximum of +1, preferably spaced at intervals or bin widths of 0.1. A bin width of 0.1 reduces the effects of noise and provides adequate definition to each rectangle formed in the histogram. A bin width of 0.1 discriminates energy levels differing by 0.1 or more while reducing the effects from noise and other artifacts typically found in energy levels less than 0.1. Choosing bin-widths greater than 0.1 such as 0.30 may result in lower resolution of energy imprints. Distribution of the normalized binned values of each depolarization is referred to as an imprint of energy distribution or energy imprint. Since the normalized levels (or the edges of the histogram bins) are the same for all beats, direct comparison of energy imprints of EGM beats can be made without the need of any alignment of the EGM beats or signals.

The y-axis or vertical axis is parsed in equal intervals that relate to frequency or percentage of occurrences in which a normalized signal falls within boundaries (or bin width) established for a particular bin. Each rectangle is formed by vertical bars along boundaries at the bin width shown on the x axis and that extend from zero of the y axis to an upper horizontal bar delineated at an occurrence number for each bin in which data is found for the normalized signal. FIGS. 4B-4C show bins along the x axis having a bin width of 0.1 that starts at −1.0 and extends to +1.0 while the frequency of occurrence starts at 0 and extends to 3.0 at 0.5 intervals. Generally, each data point from FIG. 4A can be normalized and then translated to FIG. 4B.

The binned values associated with the first depolarization are compared to the binned values associated with the second depolarization at block 322. A simple correlation analysis is employed in order to compare two energy imprints. An exemplary correlation analysis involves calculating a correlation coefficient and then determining the degree of similarity at block 335 that exists between the energy imprints. The correlation coefficient equation is as follows:

$$R = (N\Sigma XY - \Sigma X\Sigma Y)*100\% / \sqrt{[(N\Sigma X^2 - (\Sigma X)^2)(N\Sigma Y^2 - (\Sigma Y)^2)]}$$

where:

R is the correlation coefficient;

N is a total number of bins used to represent each depolarization (e.g. number of bins spanning from −1 to +1 at intervals of 0.1 yields N=20 bins for each depolarization event);

X is the number of elements in each bin for the first energy imprint related to the first depolarization (first beat); and Y is the number of elements in each bin for the second energy imprint related to the second depolarization or second beat.

The bins are pre-defined by a user (e.g. programmer, medical personnel such as a doctor etc.) and are stored in the memory to be retrieved by the microprocessor 224 for computing the energy imprints of each beat. Generally, data collected from each energy imprint is stored in memory and then accessed by microprocessor 224 in order to calculate R. Similar depolarizations or signals exhibit similar energy imprints; and, since the histograms are constructed with the same bins, the energy imprints of two depolarizations or signals can be compared without the need to shift and align the signals. Elimination of shifting and aligning signals can substantially reduce computations and analysis by the IMD 100, which, in turn, reduces the energy (e.g. battery, capacitor etc.) consumed by the IMD 100.

At block 324, a determination is made as to whether the first depolarization is substantially similar to the second depolarization. Similarity between the first and second energy imprints is based on R which is calculated using the binned data and the equation for R. If R is greater than a predetermined threshold such as 65 percent (%), a substantial similarity exists between the first and second energy imprints. No similarity exists if 65% between first and second energy imprints. If the binned values associated with the first and second depolarizations are not similar, the NO path is followed to block 328, described below. If the binned values associated with the first and second depolarizations are similar, then the YES path to block 326 is followed which is a counter that tracks or keeps a count of the number of beat pair matches. The counter is designated as MATCH=MATCH+1. MATCH is initially cleared to zero before beats from a tachyarrhythmia episode are compared to a template depolarization or template beat which is another beat of the same episode. Thereafter, MATCH is incremented by 1 for each time a match results from a beat-pair comparison where the criteria of match is as described above. At block 328, a comparison counter is encountered that counts the number of comparisons that are performed between beat-pairs of a tachyarrhythmia episode. The comparison counter is incremented by 1 every time a beat to beat comparison is performed. The comparison counter is designated as COMPARISON COUNTER=COMPARISON COUNTER+1. After incrementing the comparison counter, block 330 is encountered where the decision whether adequate number of comparisons have been made is taken. For example, adequate number of beat-beat comparisons may be 5, where every alternate beats within a tachyarrhythmia episode are compared. In this example, the Nth beat of the episode is compared with (N-2)th beat in the first comparison, (N-2)th beat is compared with (N-4)th beat in the second comparison, (N-4)th beat with (N-6)th beat in the third comparison, (N-6)th beat with (N-8)th beat in the fourth comparison and (N-8)th beat with (N-10)th beat in the fifth comparison where N>10. The Nth beat may be the detection beat. The detection beat is the beat at which a tachyarrhythmia is detected according to the programmed tachyarrhythmia detection criteria, as previously discussed. If adequate number of comparisons are not made, the NO path is followed to block 316 to compare more beat-pairs from the tachyarrhythmia episode. If adequate number of comparisons have been made, the YES path is followed to block 332 in which the number of beat-pair matches are compared against a threshold. For example, if the adequate number of beat-pair comparisons is set to 5, the threshold may be set to 3. If the number of matches equal or exceed the threshold, the tachyarrhythmia is classified as monomorphic VT (block 334) and treated with appropriate therapy e.g. painless anti-tachycardia pacing (block 336). If the number of beat to beat matches is less than the threshold, the tachyarrhythmia is classified as a polymorphic VT (block 340) and a different therapy (e.g. shock) is delivered accordingly (block 342).

One or more aspects of the algorithm presented in FIG. 3 have been determined to be highly accurate at identifying monomorphic VTs versus polymorphic VTs. MIRACLE and PAINFREE2 are publically available databases that include exemplary data related to monomorphic VTs and polymorphic VTs. The present disclosure was able to accurately identify 449 out of 496 monomorphic VTs, which indicates that the present disclosure has monomorphic VT sensitivity (polymorphic VT/VF specificity) of about 90.52% while polymorphic VT/VF sensitivity is equal to 96.5%.

Numerous examples are presented below to show the manner in which monomorphic VT and polymorphic VT/VF are discriminated from each other. FIGS. 4A-4C, 9A-9C, 10A-10C, and FIGS. 11A-11C exemplify monomorphic beats while FIGS. 5-8A-C exemplify polymorphic beats. FIGS. 4A-4C depict one embodiment of the present disclosure in which more than five heartbeat comparisons are used to determine that a patient is experiencing a monomorphic VT episode. In this embodiment, the depolarization or heartbeat is sensed by one or more of the electrodes on lead 120. The y-axis represents the potential difference (e.g. voltage) of the EGM signal (in mV), x-axis represents number of samples. Each window contains 25 samples, centered about the time of sensing, where the sampling rate is 128 Hz.

First and second heartbeats 402, 404 or depolarizations are shown, in analog form, in FIG. 4A. The first heartbeat was sampled and is referred to as heartbeat 2 while the second selected heart beat is referred to as heart beat 4. The p-p amplitudes of the first and second depolarizations 402, 404 are computed and compared by microprocessor 224.

The first depolarization 402 possesses a positive peak=4.97 and a negative peak=−6.36. Therefore, the p-p amplitude for first depolarization 402 is as follows:

p-p amplitude1=(4.97+6.36)=11.33

Similarly, the second depolarization 404 possesses a positive peak=4.56 and a negative peak=−6.06. Therefore, the p-p amplitude second depolarization 404 is as follows:

p-p amplitude2=(4.56+6.06)=10.62

The microprocessor 224 then computes the percent relative difference for p-p amplitudes between the first and second depolarizations 402, 404. The equation for the percent relative difference is as follows:

Percent relative difference in *p-p* amplitude=|*p-p* amplitude1−*p-p* amplitude 2|/lesser(*p-p* amplitude1,*p-p* amplitude 2).

Therefore, with respect to the first and second depolarizations 402, 404, the percent relative difference in p-p amplitude= (11.33−10.62)/10.62*100=6.69.

The microprocessor 224 then determines whether the percent relative difference for peak to peak (p-p) amplitudes is less than a predetermined threshold. In one embodiment, it is preferable to set the threshold at 20, which conservatively establishes similarity between the first and second depolarizations 402, 404. If the percent relative difference is equal to or above 20, the first and second depolarizations 402, 404 are deemed different, which causes the microprocessor 224 to select another beat-pair from the EGM signal to compare. However, since the percent relative difference is 6.11, which is well below 20, the p-p amplitudes of the first and second depolarizations 402, 404 are deemed similar. Since the p-p amplitudes of the first and second depolarizations 402, 404 are deemed similar, each normalized depolarization is decomposed into a predetermined number of bins. For example, the predetermined number of bins can be set at 20. Therefore, the bins are parsed or decomposed as follows: −1 to −0.9, −0.9 to −0.8, −0.8 to −0.7, −0.7 to −0.6, −0.6 to −0.5, −0.5 to −0.4, −0.4 to −0.3, −0.3 to −0.2, −0.2 to −0.1, −0.1 to 0, 0 to 0.1, 0.1 to 0.2, 0.2 to 0.3, 0.3 to 0.4, 0.4 to 0.5, 0.5 to 0.6, 0.6 to 0.7 0.7 to 0.8, 0.8 to 0.9 and 0.9 to 1. A histogram of the normalized amplitudes of the first depolarization is then formed, as shown in FIG. 4B. As applied to FIG. 4B, the number of elements in each bin in order are X=[3 2 1 2 0 2 1 0 3 0 0 1 3 1 1 2 2 1 0 0].

A histogram of the normalized amplitudes of the second depolarization is then formed, as shown in FIG. 4C. As applied to FIG. 4C, the number of elements in each bin in order are Y=[3 2 1 2 0 2 1 1 2 0 0 1 2 2 2 1 2 1 0 0].

Thereafter, a correlation coefficient is computed at 85.09% by microprocessor 224. Each component that is a part of the correlation coefficient R equation has been calculated as follows:

$$\sum X^2 = 53, \sum X = 25, \sum Y^2 = 47, \sum Y = 25,$$
$$\sum XY = 47, N = 20;$$

$$R = \frac{(N\sum XY - \sum X \sum Y)*100\%}{\sqrt{\left[\begin{array}{c}(N\sum X^2 - (\sum X)^2)\\(N\sum Y^2 - (\sum Y)^2)\end{array}\right]}}$$
$$= \frac{(20*47 - 25*25)*100\%}{\sqrt{[(20*53 - (25)^2)(20*47 - 25^2)]}}$$
$$= 31500 / \sqrt{(435*315)}$$
$$= 85.09\%$$

The correlation coefficient, computed at 85.09%, is greater than a predetermined threshold of 65% which means, a match exists between the first and a second depolarizations 402, 404, as would be expected between beats of a monomorphic VT episode.

Figure 5:
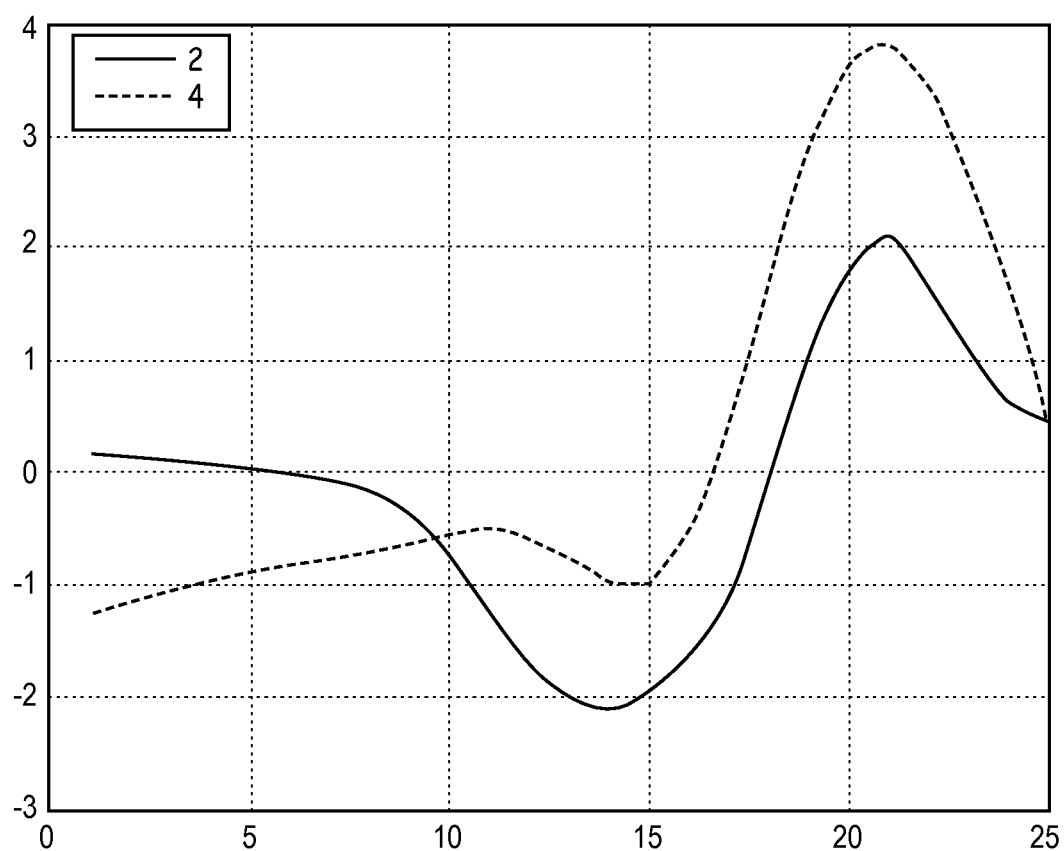
FIG. 5 is a graph of two weighted depolarizations of a polymorphic VT episode.

Example 2, depicted in FIG. 5, relates to a polymorphic VT episode that was solely determined by merely evaluating the difference in p-p amplitudes between first and second depolarizations 402, 404. To evaluate the difference in p-p amplitudes between first and second depolarizations 402, 404, a calculation is made as to percent (%) relative difference between the p-p amplitudes. As to the first depolarization (beat 2), the positive peak=2.16 and the negative peak=−2.12. The p-p amplitude=(2.16+2.12)=4.28

As to the second depolarization (beat 4), the positive peak=3.45 and the negative peak=−1.79.

The *p-p* amplitude is=(3.45+1.79)=5.24% relative difference in *p-p* amplitude=[(*p-p* amplitude for beat 2−*p-p* amplitude for beat 4)/lesser of(*p-p* amplitude for beat 2,*p-p* amplitude for beat 4)

As applied to the data, % relative difference in *p-p* amplitude=(5.24−4.28)/4.28*100=22.43>20

The predetermined threshold is set at 20.

Since the percent relative difference exceeds the predetermined threshold of 20, the first and second depolarizations are different and do not match. Accordingly, it is unnecessary to proceed to comparing energy imprints.

Figure 6B:
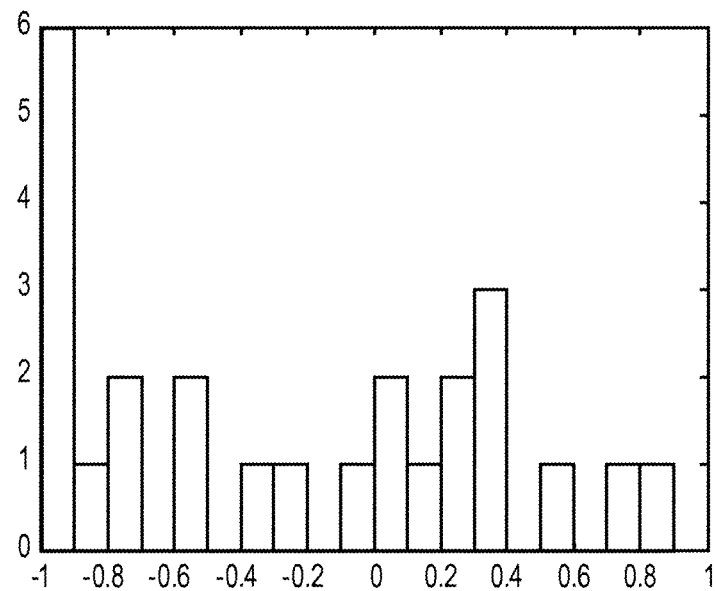
FIG. 6B is a graph of an energy imprint of the first depolarization depicted in FIG. 6A.
Figure 6C:
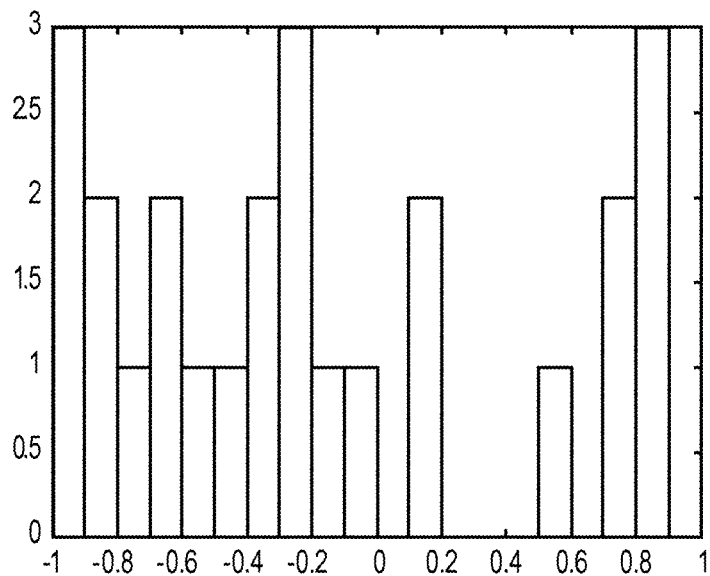
FIG. 6C is a graph of an energy imprint of the second depolarization depicted in FIG. 6A.

FIGS. 6A-6C present a third example that relates to two beats of a polymorphic VT episode. As shown in FIG. 6A, the first and second weighted depolarizations have generally similar positive and negative peaks. The first depolarization (beat 2) has a positive peak=3.08 and a negative peak=−3.54.

The p-p amplitude=(3.08+3.54)=6.62

The second depolarization(beat 4) has a positive peak=3.64 and a negative peak=−4.11. The p-p amplitude=(3.64+4.11)=7.75

The percent relative difference in p-p amplitude=(7.75−6.62)/6.62*100=17.07<20 (threshold). Since the percent relative difference is less than 20, the energy imprints of the first and second depolarizations are computed and then compared.

Each normalized depolarization or beat is decomposed into 20 bins shown in FIGS. 6B-6C. Along the x axis, each bin has a bin width of 0.10. The bins are adjacent and placed between −1 to −0.9, −0.9 to −0.8, −0.8 to −0.7, −0.7 to −0.6, −0.6 to −0.5, −0.5 to −0.4, −0.4 to −0.3, −0.3 to −0.2, −0.2 to −0.1, −0.1 to 0, 0 to 0.1, 0.1 to 0.2, 0.2 to 0.3, 0.3 to 0.4, 0.4 to 0.5, 0.5 to 0.6, 0.6 to 0.7, 0.7 to 0.8, 0.8 to 0.9 and 0.9 to 1.

A normalized amplitude histogram is formed of first depolarization (beat 2) shown in FIG. 6B. The number of elements in order of each bin is provided by X, as provided below.
X=[6 1 2 0 2 0 1 1 0 1 2 1 2 3 0 1 0 1 1 0]

A normalized amplitude histogram is formed of the second depolarization 404 (beat 4).

The number of elements in order of each bin is as follows:
Y=[32 1 2 1 1 2 3 1 1 0 2 0 0 0 1 0 2 3 0].

The correlation coefficient was determined to be 23.6% which is much lower than the predetermined threshold of 65%. Therefore, the beats do not match.

A fourth example relates to two different looking beats of a PVT episode. The first beat (FIG. 7A) is a template beat derived from the same episode from which the second beat is sampled. The second beat (FIG. 8A) is then compared to the first beat. The first beat and second beats are normalized, as shown in FIGS. 7B and 8B, respectively. The energy imprints for the first and second beats, are computed based on maximum and minimum normalized values and are displayed in FIGS. 7C and 8C. The similarity of energy imprints are compared through the simple correlation coefficient calculation, which was determined to be equal to −8.5%. Since −8.5% is below 65%, a match does not exist between the first and second beats.

A fifth example is presented in FIGS. 9A-9C that relates to two beats of a MVT episode. FIG. 9A depicts a template beat (first beat) as sensed from a medical electrical lead. The sensed electrical signal undergoes the normalization process resulting in the normalized signal which is shown in FIG. 9B and binned in FIG. 9C. The height of each rectangle represents the number of samples that fall within a certain range. The first bin in FIG. 9C represents the number of samples in FIG. 9B that fall within −1 to −0.9. Samples with values −0.93 or −0.94 or −0.95 are also counted in the first bin. The energy imprint is computed in which elements of the beat are binned as shown in FIG. 9C.

FIGS. 10A-10C depict another beat (second beat) that is normalized, (FIG. 10B). The energy imprint is computed. The elements of the beat are binned as shown in FIG. 10C. The correlation coefficient was calculated between the first and second depolarizations as 96%, which exceeds the threshold of 65%; therefore, the beats match.

A sixth example is presented in FIGS. 11A-11C that relates to two beats of a MVT episode. First and second normalized depolarizations is shown in FIG. 11A. Each normalized depolarization or beat is then decomposed into 20 bins shown in FIGS. 11B-11C. Along the x axis, each bin has a bin width of 0.10. The bins are adjacent and placed between −1 to −0.9, −0.9 to −0.8, −0.8 to −0.7, −0.7 to −0.6, −0.6 to −0.5, −0.5 to −0.4, −0.4 to −0.3, −0.3 to −0.2, −0.2 to −0.1, −0.1 to 0, 0 to 0.1, 0.1 to 0.2, 0.2 to 0.3, 0.3 to 0.4, 0.4 to 0.5, 0.5 to 0.6, 0.6 to 0.7 0.7 to 0.8, 0.8 to 0.9 and 0.9 to 1.

A normalized amplitude histogram is formed of first depolarization (beat 2) shown in FIG. 6B. The number of elements in order of each bin is provided by X, as provided below.
X=[3 1 2 1 1 1 1 8 0 0 1 0 1 0 1 4 0 0 0 0]

A normalized amplitude histogram is formed of the second depolarization 404 (beat 4).

The number of elements in order of each bin is as follows:
Y=[3 1 2 1 1 1 1 8 0 0 1 0 1 0 1 0 1 2 2 0 0].

The correlation coefficient was determined to be 23.6% which is much lower than the predetermined threshold of 65%. Therefore, the beats do not match. The correlation coefficient was calculated as 94.9%, which exceeds 65%; therefore, the beats do match.

A seventh example is presented in FIGS. 12A-12C which relates to two normalized beats of a PVT episode. Each normalized depolarization or beat is decomposed into 20 bins shown in FIGS. 12B-12C. Along the x axis, each bin has a bin width of 0.10. The bins are adjacent and placed between −1 to −0.9, −0.9 to −0.8, −0.8 to −0.7, −0.7 to −0.6, −0.6 to −0.5, −0.5 to −0.4, −0.4 to −0.3, −0.3 to −0.2, −0.2 to −0.1, −0.1 to 0, 0 to 0.1, 0.1 to 0.2, 0.2 to 0.3, 0.3 to 0.4, 0.4 to 0.5, 0.5 to 0.6, 0.6 to 0.7 0.7 to 0.8, 0.8 to 0.9 and 0.9 to 1.

A normalized amplitude histogram is formed of first depolarization (beat 2) shown in FIG. 12B. The number of elements in order of each bin is provided by X, as provided below.
X=[2 2 0 2 2 2 1 1 0 3 1 0 2 1 3 4 1 0 0 0]

A normalized amplitude histogram is formed of the second depolarization 404 (beat 4).

The number of elements in order of each bin is as follows:
Y=[3 1 1 0 1 1 1 1 0 1 1 1 4 1 2 1 2 3 0 0].

The correlation coefficient was determined to be 23.4% which is much lower than the predetermined threshold of 65%. Therefore, the beats do not match.

While the present disclosure employs a preferred threshold of percent relative difference for peak to peak amplitudes is less than 20% and a R greater than a predetermined threshold such as 65 percent other applicable ranges can be used. For example, another embodiment could be determining that monomorphic VT is present if three or more beat pairs have a relative difference in peak-to-peak amplitudes less than or equal to 15% and a correlation coefficient between their respective energy imprints is greater than 75%. In yet another embodiment, monomorphic VT is present if three or more beat pairs have a relative difference in peak-to-peak amplitudes less than or equal to 40% and a correlation coefficient between their respective energy imprints is greater than 60%. Generally, the disclosure herein covers any embodiment that determines the tachyarrhythmia to be monomorphic VT if three or more beat pairs have a relative difference in peak-to-peak amplitudes less than a threshold which lies between 15-40% and a correlation coefficient between their respective energy imprints is greater than a value which lies between 60-90%.

As shown by the examples and the flow diagram presented in FIG. 3, the present disclosure determines types of heart rhythms by comparing pairs of beats or depolarizations without shifting and aligning the normalized digital values associated with the pairs. Each comparison involves one depolarization or beat from the tachyarrhythmia episode and another beat of the same episode or a template beat derived from signals indicative of a heart depolarization of a known type. Additionally, fewer comparisons between depolarizations or heart beats need to be performed in order to determine the type of VT present in a patient. For example, only five beat to beat comparisons needs to be performed to reliably discriminate monomorphic VT from polymorphic VT/VF or discriminate SVT from VT. A more detailed description of a method to discriminate SVT from VT is described in a co-pending U.S. patent application Ser. Nos 61/513,653 and 13/561,967 filed by Subham Ghosh et al. on the same day as the present application, the disclosures of which are incorporated herein in their entirety. Accordingly, the present disclosure provides an alternative method of easily and reliably determining a type of heart rhythm. Various examples of this disclosure have been described. These and other examples are within the scope of the following claims.

The invention claimed is:

1. A method of treating heart rhythms comprising:
sensing electrical signals associated with depolarizations of a patient's heart;
converting the sensed electrical signals to digital values and storing the digital values;
normalizing the stored digital values associated with at least a pair of depolarizations of the patient's heart;
binning the normalized digital values associated with the depolarizations;
comparing the binned values associated with one depolarization to the binned values associated with another depolarization in the pair of depolarizations; and
using a result of the comparison to select and deliver a therapy.

2. The method of claim 1 wherein the selected therapy is directed to treating heart rhythms related to one of monomorphic ventricular tachycardia (VT), and polymorphic VT.

3. The method of claim 2 further comprising:
determining the selected therapy without shifting and aligning the normalized digital values associated with one of the depolarizations to the normalized digital values associated with another depolarization.

4. The method of claim 2 wherein the binned values are digitized samples of the signal associated with each depolarization.

5. The method of claim 1 further comprising:
comparing peak-to-peak amplitudes of one depolarization and another depolarization; and
determining whether the peak-to-peak amplitudes of one depolarization and another depolarization in each pair have a relative difference of less than or equal to 20%.

6. The method of 5 further comprising:
determining similarity exists between one depolarization and another depolarization of the pair of depolarizations responsive to determining if their peak-to-peak amplitudes have a relative difference of less than 20%.

7. The method of 6 further comprising:
determining whether the peak-to-peak amplitudes of the one depolarization and another depolarization of the pair of depolarizations have a relative difference of less than or equal to 20%, and
determining a correlation coefficient between an energy imprint for one depolarization and an energy imprint for another depolarization of the pair of depolarizations is less than or equal to 65%.

8. The method of claim 7 further comprising:
defining a first beat pair comprising the Nth and (N-2)th depolarizations;
defining a second beat pair comprising (N-2)th and (N-4) depolarizations;
defining a third beat pair comprising (N-4)th and (N-6)th depolarizations;
defining a fourth beat pair comprising (N-6)th and (N-8)th depolarizations;
defining a fifth beat pair comprising (N-8)th and (N-10)th depolarizations;
wherein the first through fifth beat pairs relate to an episode, N>10 and the Nth beat is the detection beat of the episode,
determining whether three or more beat pairs have a relative difference in peak-to-peak amplitudes less than or equal to 20% and a correlation coefficient between their respective energy imprints are greater than 65%.

9. The method of claim 8 wherein solely five or less beat-pair comparisons are performed to reliably select the therapy to be delivered.

10. The method of claim 8 further comprising:
detecting monomorphic VT if three or more beat pairs have a relative difference in peak-to-peak amplitudes less than or equal to 20% and a correlation coefficient between their respective energy imprints greater than 65%.

11. The method of claim 8 further comprising:
detecting polymorphic VT/VF if more than three of five beat pairs have relative difference in peak-to-peak amplitudes greater than 20% or correlation coefficient between their respective energy imprints less than or equal to 65%.

12. The method of 6 further comprising:
determining the energy imprint of one depolarization and the energy imprint of another depolarization in the pair of depolarizations;
comparing the energy imprint of the one depolarization to the energy imprint of another depolarization in the pair; and
determining whether the correlation coefficient exceeds 65% between the energy imprint of the one depolarization to the energy imprint of the other depolarization in the pair.

13. The method of 1 further comprising:
determining that a difference exists between one depolarization and another depolarization of the pair of depolarizations responsive to determining that the peak-to-peak amplitudes of the first and second depolarizations in the pair have a relative difference exceeding 20%.

14. A method of treating heart rhythms, comprising:
sensing electrical signals associated with depolarizations of a patient's heart;
converting the sensed electrical signals to digital values, and storing the digital values associated with each depolarization;
determining whether to deliver therapy to the patient;
(a) comparing a first and a second depolarization of a pair of depolarizations,
(b) determining whether the first and second depolarizations in the pair depolarizations exhibit a relative difference in peak-to-peak amplitudes of less than or equal to 20%;
(c) normalizing and binning the normalized digitized values associated with each depolarization into pre-defined bins;
(d) determining whether the correlation coefficient between the respective binned values associated with each pair of depolarization is greater than 65%;
(e) repeating operations (a) through (d) for three or more pairs of depolarizations of an episode; and
using a result of the comparisons above, selecting a therapy and delivering it to the patient.

15. The method of claim 14 wherein the selected therapy is directed to treating heart rhythms including one of supraventricular tachycardia, ventricular tachycardia (VT), monomorphic VT, and polymorphic VT.

16. The method of 15 further comprising:
determining the first and second depolarizations in a pair are similar responsive to determining if their peak-peak amplitudes have a relative difference of less than or equal to 20%, and the correlation coefficient between their respective energy-imprints is greater than 65%.

17. A method of treating heart rhythms, comprising:
sensing electrical signals associated with depolarizations of a patient's heart;
converting the sensed electrical signals to digital values, and storing the digital values associated with each depolarization;
normalizing and binning the digitized values associated with each depolarization into pre-defined bins;
comparing peak-to-peak amplitudes and binned values between pairs of depolarizations;
determining whether the two depolarizations in a pair have a relative difference in peak-to-peak amplitudes of less than or equal to 20%;
determining if the correlation coefficient between the respective binned values in a pair is greater than 65%; and
using a result of the comparisons above, selecting a therapy and delivering it to the patient.

18. A method of treating heart rhythms, comprising:
normalizing a signal associated with one beat of a tachyarrhythmia episode;
computing an imprint of energy distribution using the normalized signal; and
comparing the imprint of energy distribution to that of a normalized signal derived from another beat of the same episode or a normalized signal associated with depolarization of a known type.

19. A method of treating heart rhythms comprising:
sensing electrical signals associated with depolarizations of a patient's heart;
converting the sensed electrical signals to digital values and storing the digital values;
normalizing the stored digital values associated with at least first and second depolarizations of the patient's heart;
binning the normalized digital values associated with the first and second depolarizations into pre-defined bins;
comparing peak-to-peak amplitude of the first depolarization to peak-to-peak amplitude of the second depolarization;
comparing the binned values associated with the first depolarization to the binned values associated with the second depolarization;
using a result of the comparisons to select and deliver a therapy,
wherein the selected therapy is directed to treating one of monomorphic VT and polymorphic VT.

20. An article comprising a computer readable medium having instructions stored thereon, which when executed, causes:
sensing electrical signals associated with depolarizations of a patient's heart;
converting the sensed electrical signals to digital values and storing the digital values;
normalizing the stored digital values associated with at least a pair of depolarizations of the patient's heart;
binning the normalized digital values associated with each depolarization into pre-defined bins;
comparing the peak-to-peak amplitude of the first depolarization to peak-to-peak amplitude of the second depolarization;
comparing the binned values associated with one depolarization to the binned values associated with another depolarization in the pair of depolarizations; and
using a result of the comparisons to select and deliver a therapy.

21. The article of claim 20 wherein the selected therapy is directed to treating one of monomorphic VT and polymorphic VT.

22. The article of claim 21 further comprising:
determining the selected therapy using a result of morphologic comparison between pairs of depolarizations without shifting and aligning the normalized digital values associated with one depolarizations to those associated with another depolarization in each pair.

23. The article of claim 21 wherein the binned values are normalized digitized samples of the signal associated with each depolarization.

24. The article of claim 20 further comprising:
comparing peak-to-peak amplitudes between pairs of depolarizations; and
determining whether the peak-to-peak amplitudes of one depolarization and another depolarization in a pair have a relative difference of less than or equal to 20%.

25. A system for detecting and treating a cardiac condition comprising:
means for sensing electrical signals associated with depolarizations of a patient's heart;
means for converting the sensed electrical signals to digital values and storing the digital values;
means for normalizing the stored digital values associated with at least a pair of depolarizations of the patient's heart;
means for comparing the peak-to-peak amplitude of one depolarization to peak-to-peak amplitude of another depolarization in each pair
means for binning the normalized digital values associated with the depolarizations into pre-defined bins;
means for comparing the binned values associated with one depolarization to the binned values associated with another depolarization in the pair of depolarizations; and
means for using a result of the comparison of the peak-to-peak amplitudes and binned values associated with solely five or less number of depolarization-pairs to select and deliver a therapy.

26. The system of claim 25 wherein the selected therapy is directed to treating heart rhythms related to one of monomorphic VT, and polymorphic VT.

27. A method of treating heart rhythms comprising:
sensing electrical signals associated with depolarizations of a patient's heart;
converting the sensed electrical signals to digital values and storing the digital values;
normalizing the stored digital values associated with at least a pair of depolarizations of the patient's heart; and
binning the normalized digital values associated with the depolarizations into pre-defined bins.

28. The method of claim 27 wherein distribution of the normalized binned values of each depolarization is an imprint of energy distribution.

29. The method of claim 28 further comprising:
determining the selected therapy using a result of morphologic comparison between pairs of depolarizations without shifting and aligning the normalized digital values associated with one of the depolarizations to those associated with another depolarization in each pair.

30. The method of claim 28 wherein the binned values are the normalized digitized samples of the signal associated with each depolarization.

31. The method of claim 28 further comprising comparing the energy imprint associated with one depolarization to an energy imprint associated with another depolarization in the pair of depolarizations; and
using a result of the comparison to select and deliver a therapy.

32. The method of claim 27 wherein the selected therapy is directed to treating heart rhythms one of supraventricular tachycardia, ventricular tachycardia (VT), monomorphic VT, and polymorphic VT.

33. The method of claim 27 further comprising:
comparing peak-to-peak amplitudes between pairs of depolarizations; and
determining whether the peak-to-peak amplitudes of one depolarization and another depolarization in a pair have a relative difference of less than or equal to 20%.

34. The method of 33 further comprising:
determining the one depolarization and the another depolarization in the pair are similar responsive to determining if their peak-peak amplitudes have a relative difference of less than or equal to 20%, and
determining a correlation coefficient between their respective energy-imprints is greater than 65%.

35. The method of 34 further comprising:
determining that the two depolarizations in a pair are different responsive to determining that the peak-to-peak amplitudes of the first and second depolarizations in the pair have a relative difference exceeding 20%, or if the peak-to-peak amplitudes of the first and second depolarizations have a relative difference of less than or equal to 20%, and the correlation coefficient between their respective energy-imprints is less than or equal to 65%.

36. The method of 35 further comprising:
determining imprints of energy distribution of the two depolarizations in a pair;
comparing the imprint energy distribution of one depolarization to the imprint of energy distribution of the other depolarization in the pair; and
determining whether the correlation coefficient between the respective energy imprints exceeds 65%.

37. The method of claim 36 further comprising:
defining a first depolarization pair comprising the Nth and (N-2)th depolarizations
defining a second depolarization pair comprising (N-2)th and (N-4) depolarizations
defining a third depolarization pair comprising (N-4)th and (N-6)th depolarizations
defining a fourth depolarization pair comprising (N-6)th and (N-8)th depolarizations
defining a fifth depolarization pair comprising (N-8)th and (N-10)th depolarizations,
wherein the first through fifth depolarization pairs relate to an episode, N>10 and the Nth depolarization is the detection depolarization of the episode;
determining whether three or more depolarization pairs have a relative difference in peak-to-peak amplitudes less than or equal to 20%; and
determining a correlation coefficient between their respective energy imprints greater than 65%.

38. The method of claim 37 wherein solely five or less depolarization-pair comparisons are performed to reliably select the therapy to be delivered.

39. The method of claim 38 further comprising:
detecting monomorphic VT if three or more depolarization pairs have a relative difference in peak-to-peak amplitudes less than or equal to 20%; and
determining a correlation coefficient between their respective energy imprints greater than 65%.

40. The method of claim 39 further comprising:
detecting polymorphic VT/VF if more than three of five depolarization pairs have relative difference in peak-to-peak amplitudes greater than 20% or correlation coefficient between their respective energy imprints less than or equal to 65%.

* * * * *

UNITED STATES PATENT AND TRADEMARK OFFICE
CERTIFICATE OF CORRECTION

| | | |
|---|---|---|
| PATENT NO. | : 8,750,994 B2 | Page 1 of 2 |
| APPLICATION NO. | : 13/562039 | |
| DATED | : June 10, 2014 | |
| INVENTOR(S) | : Subham Ghosh et al. | |

It is certified that error appears in the above-identified patent and that said Letters Patent is hereby corrected as shown below:

In The Claims

Col. 17, line 45, delete "The method of 5 further comprising" and insert in place thereof -- The method of claim 5, further comprising --;

Col. 17, line 50, delete "The method of 6 further comprising" and insert in place thereof -- The method of claim 6, further comprising --;

Col. 18, line 25, delete "The method of 6 further comprising" and insert in place thereof -- The method of claim 6, further comprising --;

Col. 18, line 36, delete "The method of 1 further comprising" and insert in place thereof -- The method of claim 1, further comprising --;

Col. 19, line 3, delete "The method of 15 further comprising" and insert in place thereof -- The method of claim 15, further comprising --;

Col. 19, line 5, delete "if their peak-peak amplitudes have a" and insert in place thereof -- if their peak-to-peak amplitudes have a --;

Col. 19, line 46, delete "An article comprising a computer readable" and insert in place thereof -- An article comprising a computer-readable --;

Col. 20, line 38, delete "another depolarization in each pair" and insert in place thereof -- another depolarization in each pair; --;

Col. 21, line 22, delete "The method of 33 further comprising" and insert in place thereof -- The method of claim 33, further comprising --;

Signed and Sealed this
Eighth Day of March, 2016

Michelle K. Lee
*Director of the United States Patent and Trademark Office*

Col. 21, line 25, delete "determining if their peak-peak- amplitudes" and insert in place thereof -- determining if their peak-to-peak amplitudes --;

Col. 21, line 29, delete "The method of 34 further comprising:" and insert in place thereof -- The method of claim 34, further comprising --;

Col. 21, line 38, delete "The method of 35 further comprising:" and insert in place thereof -- The method of claim 35, further comprising: --;

Col. 22, line 8, delete "(N-2)th depolarizations" and insert in place thereof -- (N-2)th depolarizations; --;

Col. 22, line 10, delete "an d (N-4) depolarizations" and insert in place thereof -- an d (N-4) depolarizations; --;

Col. 22, line 12, delete "(N-6)th depolarizations" and insert in place thereof -- (N-6)th depolarizations; --;

Col. 22, line 14, delete "and (N-8)th depolarizations" and insert in place thereof -- and (N-8)th depolarizations; --;